(12) United States Patent
Borden et al.

(10) Patent No.: US 7,064,822 B2
(45) Date of Patent: Jun. 20, 2006

(54) EVALUATING A MULTI-LAYERED STRUCTURE FOR VOIDS

(75) Inventors: Peter G. Borden, San Mateo, CA (US); Ji-Ping Li, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 11/114,300

(22) Filed: Apr. 25, 2005

(65) Prior Publication Data

US 2005/0186776 A1    Aug. 25, 2005

Related U.S. Application Data

(62) Division of application No. 10/090,262, filed on Mar. 1, 2002, now Pat. No. 6,885,444.

(51) Int. Cl.
*G01N 21/88* (2006.01)
(52) U.S. Cl. .............. 356/239.8; 356/237.4; 356/237.5; 356/630
(58) Field of Classification Search .. 356/237.1–237.6, 356/239.8, 505, 630–632; 250/559.27, 559.28, 250/559.39, 559.41, 252.1
See application file for complete search history.

(56) References Cited

U.S. PATENT DOCUMENTS

| | | | | |
|---|---|---|---|---|
| 3,462,602 A | 8/1969 | Apple | ......................... | 250/83 |
| 4,255,971 A | 3/1981 | Rosencwaig | ................ | 73/606 |
| 4,468,136 A | 8/1984 | Murphy et al. | ............... | 374/45 |
| 4,521,118 A | 6/1985 | Rosencwaig | .................... | 374/5 |
| 4,522,510 A | 6/1985 | Rosencwaig et al. | ......... | 374/7 |
| 4,579,463 A | 4/1986 | Rosencwaig et al. | ......... | 374/57 |
| 4,632,561 A | 12/1986 | Rosencwaig et al. | ....... | 356/432 |
| 4,634,290 A | 1/1987 | Rosencwaig | .................... | 374/5 |
| 4,636,088 A | 1/1987 | Rosencwaig et al. | .......... | 374/5 |
| 4,679,946 A | 7/1987 | Rosencwaig et al. | .......... | 374/5 |
| 4,750,822 A | 6/1988 | Rosencwaig et al. | ....... | 324/445 |
| 4,795,260 A | 1/1989 | Schuur et al. | .............. | 356/400 |
| 5,042,951 A | 8/1991 | Gold et al. | ................. | 356/369 |
| 5,149,978 A | 9/1992 | Opsal et al. | ................ | 250/234 |
| 5,181,080 A | 1/1993 | Fanton et al. | ............... | 356/381 |
| 5,228,776 A | 7/1993 | Smith et al. | ................... | 374/5 |
| 5,377,006 A | 12/1994 | Nakata | ....................... | 356/349 |

(Continued)

FOREIGN PATENT DOCUMENTS

EP    0 718 595    6/1996

(Continued)

OTHER PUBLICATIONS

J. Kolzer et al. "Thermal Imaging and Measurement Techniques for Electronic Materials and Devices" Microelectronic Engineering, vol. 31, 1996 (month unknown) pp. 251-.

(Continued)

*Primary Examiner*—Gregory J. Toatley
*Assistant Examiner*—Sang H. Nguyen
(74) *Attorney, Agent, or Firm*—Omkar Suryadevara

(57) ABSTRACT

A method and apparatus measure properties of two layers of a damascene structure (e.g. a silicon wafer during fabrication), and use the two measurements to identify a location as having voids. One of the two measurements is of resistance per unit length. The two measurements may be used in any manner, e.g. compared to one another, and voids are deemed to be present when the two measurements diverge from each other. In response to the detection of voids, a process parameter used in fabrication of the damascene structure may be changed, to reduce or eliminate voids in to-be-formed structures.

20 Claims, 17 Drawing Sheets

U.S. PATENT DOCUMENTS

| | | | |
|---|---|---|---|
| 5,436,463 A * | 7/1995 | Rostoker | 250/559.04 |
| 5,574,562 A | 11/1996 | Fishman et al. | 356/432 |
| 5,706,094 A | 1/1998 | Maris | 356/432 |
| 5,877,860 A | 3/1999 | Borden | 356/376 |
| 5,883,518 A | 3/1999 | Borden | 324/752 |
| 5,966,019 A | 10/1999 | Borden | 324/752 |
| 5,978,074 A | 11/1999 | Opsal et al. | 356/72 |
| 6,020,964 A | 2/2000 | Loopstra et al. | 356/401 |
| 6,040,936 A | 3/2000 | Kim et al. | 359/245 |
| 6,049,220 A | 4/2000 | Borden et al. | 324/765 |
| 6,054,868 A | 4/2000 | Borden et al. | 356/447 |
| 6,154,280 A | 11/2000 | Borden | 356/376 |
| 6,169,601 B1 | 1/2001 | Eremin et al. | 356/237.1 |
| 6,243,199 B1 | 6/2001 | Hansen et al. | 359/486 |
| 6,268,916 B1 | 7/2001 | Lee et al. | 356/432 |
| 6,323,951 B1 | 11/2001 | Borden et al. | 356/502 |
| 6,327,035 B1 | 12/2001 | Li et al. | 356/432 |
| 6,400,454 B1 | 6/2002 | Noguchi et al. | 356/237.3 |
| 6,426,644 B1 | 7/2002 | Borden et al. | 324/765 |
| 6,483,594 B1 | 11/2002 | Borden et al. | 356/502 |
| 6,489,801 B1 | 12/2002 | Borden et al. | 324/766 |
| 6,525,818 B1 | 2/2003 | Yin et al. | 356/369 |
| 6,559,942 B1 | 5/2003 | Sui et al. | 356/369 |
| 6,563,578 B1 * | 5/2003 | Halliyal et al. | 356/237.4 |
| 6,694,284 B1 | 2/2004 | Nikoonahad et al. | 702/155 |
| 6,812,047 B1 | 11/2004 | Borden et al. | 438/16 |
| 6,911,349 B1 | 6/2005 | Li et al. | 438/16 |
| 6,958,814 B1 | 10/2005 | Borden et al. | 356/432 |
| 2001/0015937 A1 | 8/2001 | Yamaguchi et al. | 369/13 |
| 2002/0167326 A1 | 11/2002 | Borden et al. | 324/752 |
| 2003/0165178 A1 | 9/2003 | Borden et al. | 374/5 |
| 2004/0218180 A1 | 11/2004 | Rosencwaig et al. | 356/369 |

FOREIGN PATENT DOCUMENTS

| | | |
|---|---|---|
| JP | 05006929 A | 1/1993 |
| JP | 2000-9443 A | 1/2000 |
| WO | WO 97/08536 | 3/1997 |
| WO | WO 99/64880 | 12/1999 |

OTHER PUBLICATIONS

C. Martinsons et al. "Recent progress in the measurement of thermal properties of hard coatings" Thin Solid Films, vol. 317, Apr. 1998, 455-457.

S. Wolf and R. N. Tauber, "Silicon Processing For The VLSI Era", vol. 1, 1986, pp. 388-399.

Yaozhi Hu and Sing Pin Tay, "Spectroscopic ellipsometry investigation of nickel silicide formation by rapid thermal process", J. Vac. Sci. Technology, American Vacuum Soc.

Dieter K. Schroder "Semiconductor Material And Device Characterization", John Wiley & Sons, Inc. 1990, pp. 538-561, and 458-466.

Bristow, Thomas C. and Dag Lindquist, "Surface Measurements With A Non-Contact Nomarski-Profiling Instrument", Interferometric Metrology, SPIE vol. 816, Aug. 1987.

Charles Kittel, "Introduction to Solid State Physics", Fourth Edition, John Wiley & Sons, published prior to Mar. 1, 2002, pp. 262-264.

Rolf E. Hummel, "Electronic Properties of Materials, An Introduction For Engineers", published prior to Mar. 1, 2002, pp. 137-145.

H.S. Carslaw and J.C. Jaeger, "Conduction of Heat In Solids", Second Edition, published prior to Mar. 1, 2002, pp. 64-66.

Rosencwaig, "Thermal Wave Characterization and Inspection of Semiconductor Materials and Devices", Chapter 5 (pp. 97-135), of Photoacoustic and Thermal Wave Phenomena in Semiconductors, North-Holland, 1987.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

A. Rosencwaig, "Thermal Wave Measurement of Thin-Film Thickness", 1986 American Chemical Society, pp. 182-191.

A. Rosencwaig et al., "Thin-Film Thickness Measurements with Thermal Waves", Journal De Physique, Oct. 1983, pp. C6-483—C6-489.

P. Alpern and S. Wurm, "Modulated Optical Reflectance Measurements on Bulk Metals and Thin Metallic Layers", J. Appl. Phys. 66(4), Aug. 15, 1989, pp. 1676-1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp. 120-131.

L. Chen et al., "Thermal Wave Studies of Thin Metal Films Using the Meta-Probe-A New Generation Photothermal System" 25th Review of Progress in QNDE, Snowbird, UT Jul. 19-24, 1998, pp. 1-12.

S. Ameri et al., "Photo-Displacement Imaging", Mar. 30, 1981, pp. 337-338.

A. Rosenwaig, "Process Control In IC Manufacturing With Thermal Waves", Review of Progress in Quantitative Nondestructive Evaluation, vol. 9, 1990, pp. 2031-2037.

K. Farnaam, "Measurement of Aluminum Alloy Grain Size on Product Wafers and its Correlation to Device Reliability", 1990 WLR Final Report, pp. 97-106.

B.C. Forget et al., "High Resolution AC Temperature Field Imaging", Electronic Letters Sep. 25, 1997, vol. 33 No. 20, pp. 1688-1689.

C. Paddock et al., "Transient Thermoreflectance from Metal Films", May 1986 vol. 11, No. 5 Optical Letters, pp. 273-275.

C. Paddock et al., "Transient Thermoreflectance from Metal Films", J. Appl. Phys. 60(1), Jul. 1, 1986, pp. 285-290.

Per-Eric Nordail et al. "Photothermal Radiometry", Physica Scripts, vol. 20, 659-662, 1979.

A. Rosenwaig, "Thermal Wave Monitoring and Imaging of Electronic Materials and Devices", pp. 73-109 (believed to be prior to Mar. 1, 2002).

A. Rosenwaig, "Applications of Thermal-Wave Physics to Microelectronics", VLSI Electronics, Microsturcture Science vol. 9, pp. 227-288 (believed to be prior to Mar. 1.

W. Lee Smith et al., "Voids, Notches and Micros-cracks in A1 Metallization Detected by Nondestructive Thermal Wave Imaging", Jun. 23m, 1989, pp. 211-221.

W. Lee Smith et al., Imaging of Subsurface Defects in ULSI Metalization (AI Voids SI Precipitates, Silicide Instability) and SI Substrates (D Defects), Technical Proceedings Semicon/Japan 1992, Nippon Convention Center, Japan pp. 238-246.

W. Lee Smith, "Nondestructive Thermal Wave Imaging of Voids & Microcracks in Aluminum Metallization", 1989 WLR Final Report, pp. 55-68.

W. Lee Smith, "Direct Measurement of Stress-Induced Void Growth by Thermal Wave Modulated Optical Refectance Imaging", 1991 IEEE/IRPS, pp. 200-208.

W. Lee Smith, "Evaluating Voids and Microcracks in A1 Metalization", Semiconductor International, Jan. 1990, pp. 232-237.

J. A. Batista et al., "Biased MOS-FET and Polycrystalline Silicon Tracks Investigated by Photothermal Reflectance Microscopy", pp. 468-469.

L. Chen et al., "Meta-Probe: A New Generation Photothermal System For Thin Metal Films Characterization" (believed to be prior to Mar. 1, 2002).

L. Chen et al., "Thermal Wave Studies of Thin Metal Films and Structures", (believed to be prior to Mar. 1, 2002).

9th International Conference on Photoacoustic and Photothermal Phenomena Conference Digest, Jun. 27-30, 1996 Nanjing, P.R. China, pp. 81.

R. S. Sharpe, Research Techniques in Nondestructive Testing vol. VII, Academic Press 1984, pp. 158-365.

R. L. Thomas et al., "Thermal Wave Imaging For Nondestructive Evaluation" 1982 Ultrasonic Symposium, pp. 586-590.

G. Slade Cargill III, "Electron-Acoustic Microscopy", Physics Today, Oct. 1981, pp. 27-32.

A. Rosencwaig, "Thermal Wave Microscopy", Solid State Technology, Mar. 1982, pp. 91-97.

Eric A. Ash, "Acoustical Imaging" vol. 12, Plenium Press, Jul. 19-22, 1982, pp. 61-65.

Paquin, "Properties of Metals", Handbook of Optics, vol. II, McGraw-Hill, Inc. (month unavailable), 1995, pp. 35.3-35.7.

Rosencwaig et al. "Detection of Thermal Waves Through Optical Reflectance", Appl Phys. Lett. 46, Jun. 1985, pp. 1013-1015.

Rosencwaig, "Thermal-Wave Imaging", SCIENCE, vol. 218, No. 4569, Oct. 1982, pp. 223-228.

Opsal et al. "Thermal-Wave Detection and Thin-Film Thickness Measurements with Laser Beam Deflection", Applied Optics, vol. 22, No. 20, Oct. 1983, pp. 3169-3176.

C. G. Welles et al., "High-Resolution Thermal Wave Imaging of Surface and Subsurface Defects in IC Metal Lines", Materials Research Society, SF Marriott, Apr. 27-May 1, 1992, pp. 1187-1191.

Entire File History of U.S. Appl. No. 10/090,262, including Office Actions and Amendments.

Entire File History of U.S. Appl. No. 10/090,316, including Office Actions and Amendments.

Entire File History of U.S. Appl. No. 09/974,571, including Office Actions and Amendments.

Entire File History of U.S. Appl. No. 10/090,287, including Office Actions and Amendments.

Entire File History of U.S. Appl. No. 09/521,232, including Office Actions and Amendments.

Entire File History of U.S. Appl. No. 09,788,273, including Office Actions and Amendments.

Entire File History of U.S. Appl. No. 10/722,724, including Office Actions and Amendments.

Entire File History of U.S. Appl. No. 09/095,805, including Office Actions and Amendments.

Entire File History of U.S. Appl. No. 10/984,463, including Office Actions and Amendments.

Entire File History of U.S. Appl. No. 10/813,407, including Office Actions and Amendments.

Entire File History of U.S. Appl. No. 10/979,397, including Office Actions and Amendments.

Entire File History of U.S. Appl. No. 10/996,194, including Office Actions and Amendments.

Entire File History of U.S. Appl. No. 11/120,427, including Office Actions and Amendments.

Entire File History of U.S. Appl. No. 10/977,380, including Office Actions and Amendments.

* cited by examiner

EVALUATING A MULTI-LAYERED STRUCTURE FOR VOIDS

This application is a divisional application of U.S. patent application Ser. No. 10/090,262 filed Mar. 1, 2002 now U.S. Pat. No. 6,885,444 that is incorporated by reference herein in its entirety.

CROSS-REFERENCE TO RELATED APPLICATIONS INCORPORATED HEREIN

This application is related to and incorporates by reference herein in their entirety the following commonly owned U.S. Patent Applications:

Ser. No. 09/095,805 entitled "AN APPARATUS AND METHOD FOR MEASURING A PROPERTY OF A LAYER IN A MULTILAYERED STRUCTURE", filed Jun. 10, 1998 by Peter G. Borden et al. which is now issued as U.S. Pat. No. 6,054,868;

Ser. No. 09/521,232 entitled "EVALUATING A PROPERTY OF A MULTILAYERED STRUCTURE", filed on Mar. 8, 2000 by Peter G. Borden et al.;

Ser. No. 09/544,280 entitled "AN APPARATUS AND METHOD FOR EVALUATING A WAFER OF SEMICONDUCTOR MATERIAL", filed Apr. 6, 2000 by Peter G. Borden et al., which is a continuation of Ser. No. 09/095,804 filed Jun. 10, 1998 and now issued as U.S. Pat. No. 6,049,220;

Ser. No. 10/090,287, entitled "IDENTIFYING DEFECTS IN A CONDUCTIVE STRUCTURE OF A WAFER, BASED ON HEAT TRANSFER THERETHROUGH" filed on Mar. 1, 2002 by Peter G. Borden and Ji-Ping Li; and Ser. No. 10/090,316, entitled "APPARATUS AND METHOD FOR MEASURING A PROPERTY OF A LAYER IN A MULTILAYERED STRUCTURE" filed on Mar. 1, 2002, by Peter G. Borden and Ji-Ping Li.

BACKGROUND

Damascene structures in semiconductor substrates are so-named because they consist of metal lines formed in narrow grooves, as illustrated by the structure shown at the bottom of FIG. 1. These metal lines may be of width W<0.15 µm and height H>0.5 µm, with an aspect ratio that may exceed 3:1 (ratio of height to width). The grooves may be formed within a dielectric layer that has a total thickness of 1 µm and a thickness between the bottom of the grooves and the bottom of the dielectric layer of T=0.5 µm.

Such damascene structures are typically formed in a multi-step process, of the type shown in FIG. 1. First, in step 110, photoresist layer 101 is formed on insulator layer 102 over substrate 103. Insulator 102 is a material such as silicon dioxide, and substrate 103 is silicon. In step 111, photoresist layer 101 is patterned, forming grooves 104a–f. The structure is then etched in step 112, forming grooves 105a–f in the insulator layer 102. Note that the grooves are less deep than the thickness of the insulator 102. The photoresist layer 101 is subsequently stripped. In step 113 the structure is coated with a barrier layer of a metal such as tantalum, followed by a seed layer of a metal such as copper, indicated as combined layers 105bs. The copper seed layer provides a conductive coating to allow electroplating of a thick copper layer onto the structure in step 114, that material being shown as layer 106. The seed layer may be 1000 Å thick on the surface, but only 100–200 Å thick on the walls of the grooves. Similarly, the tantalum layer may be 250 Å thick on the surface, but only 50 Å or less thick on the walls of the grooves. The tantalum layer prevents the copper from diffusing into the underlying layers; hence its name "barrier", and also improves adhesion of the copper to insulator 102. In step 115 the electroplated layer 106 is polished away, leaving a fill of copper in the grooves.

The yield of this process depends on the thickness t of each sidewall of each groove. This is a parameter called sidewall coverage. If the sidewall coverage is too thin, then the coating may be discontinuous, or even non-existent. It then acts as a poor nucleating surface for the subsequent electrodeposition of subsequent thick layer 106, causing problems such as void formation. Specifically, voids may arise if the plating process does not begin properly on one of the sidewalls. For example, filling may not start at the bottom of a groove, resulting in a "bottom" void. As another example, if a groove fills from the side, but not the bottom, then a "center" void may occur.

Such voids Va–Vc (FIG. 1) act as breaks in the metal lines 107a–107c, either preventing current flow, or constricting current flow to the point where the line locally overheats and fails. If the coating is too thick, the top of the groove may close off, preventing adequate circulation of electrodeposition electrolyte, resulting in poor filling of the grooves which can also result in voids. This problem is further aggravated as the technology advances, and the grooves become deeper and narrower.

Voids in a semiconductor wafer can be generated in other ways as well. For example, voids in the metal line can be opened during chemical mechanical polishing (CMP). Also, voids may be created between a metal line and the underlying dielectric layer due to volume contraction that occurs after annealing. Furthermore, stress- and electromigration voids typically nucleate at intersections of metallization grain boundaries and the passivation/interconnect interface, and can form as a consequence of current flowing through the line, resulting in failure that may occur months after manufacture.

A prior art method for detection of voids is to electrically probe long runs of metal lines, often after electrical stress. However, this is not useful in production because it only finds the voids long after the process has been completed. In addition, it requires contact to the product wafer, and such long runs for void testing are not readily available on product, because they require considerable wafer area.

Voids may also be seen using FIB-SEM (Focused Ion Beam Scanning Electron Microscopy). A focused ion beam mills out a section of the line, and a scanning electron microscope is used to view the section. This method is slow and destructive, and views such a small area that it is only of use in cases of extremely high void density, or if the void location has been found by other means such as electrical testing.

An article at the website http://www.micromagazine.com/archive/00/01/prods.html published in January 2000 describes a "Wafer Inspection System" available from Schlumberger of San Jose, Calif., as follows "The Odyssey 3000 uses an E-beam-based voltage-contrast technology to identify yield-killing electrical defects that are difficult to detect using optical systems. Designed for use in sub-0.15-µm processes, the system detects electrical, submicron particle, and pattern defects. Metal stringers, poly gate shorts, and copper damascene voids are also detectable. Real-time off-line defect review with simultaneous inspection eliminates the need to buy off-line inspection tools. The system accommodates 300-mm wafers and features an advanced graphical user interface to simplify recipe setup. Die-to-die comparisons also enable users to carry out rapid defect review."

However, such a system has limited application because it can only look at exposed layers. In many cases, lines with voids may be buried under a dielectric layer, and the formation of the dielectric layer may in fact have been the cause of the voids. The electron beam charges the dielectric, preventing its use in such cases. In addition, the voltage-contrast method is only of use in cases of extreme voiding, where the lines are almost completely broken. This is seldom the case; often the voids are smaller, but these small voids are critical to detect because they may grow into sources of failure due to factors described earlier, such as electromigration and stress.

SUMMARY

A method and apparatus in accordance with the invention measure properties of two layers of a damascene structure (e.g. a silicon wafer during fabrication), while scanning, and use the two scanning measurements to identify a location as having voids. The two scanning measurements can be used in any manner, although in one embodiment, the two measurements are compared to one another (either automatically by computer during the scanning or visually by an operator after the scanning). Voids are deemed to be present when the two measurements diverge from each other. The two measurements can be either of two layers that are adjacent to and in contact with one another or of layers that are separated from one another by one or more intermediate layers, depending on the embodiment. In response to the detection of voids, a process parameter used in fabrication of the damascene structure may be changed, to reduce or eliminate voids in to-be-formed structures, thereby to perform process control in real time.

BRIEF DESCRIPTION OF THE DRAWINGS

FIGS. 13B-1–13B-3 illustrate in cross-sectional views structures that generates signals 1711–1713 respectively. In FIG. 13B-1, voided regions are labeled as 1301a–1301d in FIG. 13B-1, and metal lines are labeled 1302a–1302d and the dielectric (such as silicon dioxide) is labeled 1303. The reference numbers in FIGS. 13B-2 and 13B-3 are obtained by adding 10 and 20 respectively to the corresponding numbers in FIG. 13B-1.

DETAILED DESCRIPTION

One embodiment measures (e.g. see acts 122 and 123 in FIG. 2) properties of two layers of a structure, and uses the two measured signals to determine existence of voids (see act 124). Measurements (as illustrated by signals S1 and S2 in FIG. 3) change depending on the presence and absence of voids (see the change in signals S1 and S2 in regions 131 and 132 respectively) when a scan is performed across a wafer. In the example illustrated in FIG. 3, signal S1 reduces by the amount dS1 and signal S2 increases by an amount dS2, so that a separation D1 between S1 and S2 in the presence of voids is reduced to the separation D2.

Figure 1:
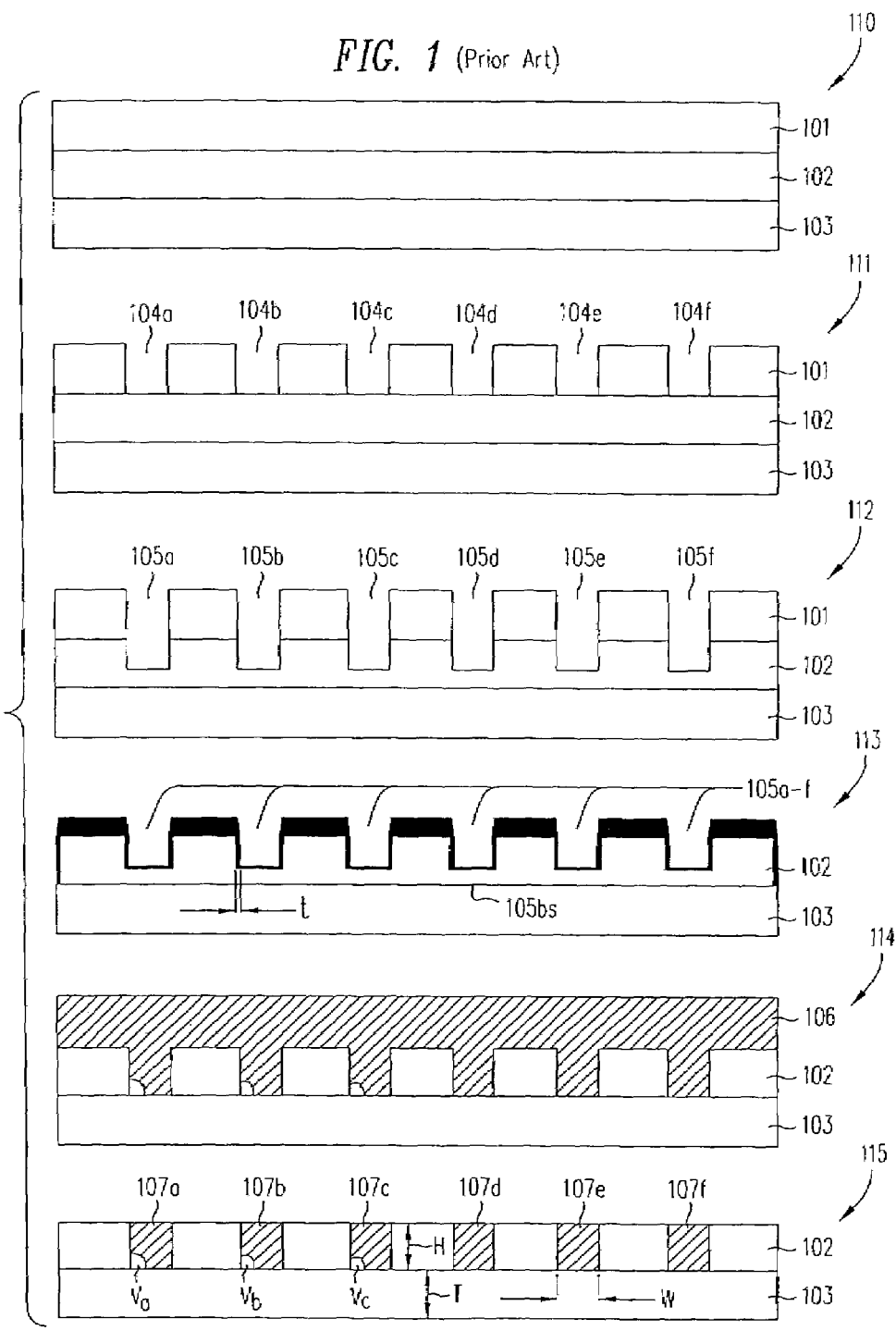
FIG. 1 illustrates structures formed in a prior art process of wafer fabrication.

The above-described acts 122–124 for finding voids are effective even in a damascene structure that is formed in the normal manner, e.g. by etching grooves in a dielectric layer and forming conductive traces (also called "lines") inside the grooves as illustrated in FIG. 1. During fabrication of the damascene structure, voids can be formed between the traces and the dielectric layer, e.g. by failure of a conductive material (that is used to form a trace) to completely fill a groove, and the above-described acts 122–124 detect such voids. In response to the detection of voids, a process parameter used in fabrication may be changed to reduce or eliminate voids in to-be-formed structures thereby to effectuate process control in real time.

Therefore, the above-described acts 122–124 detect voids in a non-destructive manner, and with high resolution when considering that such voids are often buried underneath the conductive lines, in which case they are difficult to see by conventional methods.

The above-described measurements of two signals may be used (see act 124 in FIG. 2), in any manner well known in the art, to determine existence of voids. For example, the measurements may be displayed on a screen of a computer, and a human operator may notice a change in measurements, thereby to detect voids. Depending on the embodiment and the specific example, the change from D1 to D2 (FIG. 3) can be as great as an order of magnitude, so that detecting such a change is easy. Moreover, a separation D between the two electrical signals generated in acts 122 and 123 can be plotted to obtain a two dimensional image of structure 10 (see FIG. 4) as a whole, so that the image indicates the presence and absence of voids across structure 10. Instead of a two-dimensional image, the two electrical signals from acts 122 and 123 can be themselves plotted in a graph along the y axis, with the x axis representing regions in structure 10. Note that presence/absence of voids can also be detected automatically (by a computer that monitors separation D between measurements at each location).

Specifically, divergence of the two signals can be determined by comparing separation D at various locations of a wafer under evaluation (also called "production wafer"), either in an absolute manner or in a relative manner. In one embodiment, absolute comparison is performed as follows: voids are deemed to exist at a location if separation D of the two signals is greater than a predetermined amount Dmax, which is determined from test wafers (which are wafers known to have voids and wafers known to have no voids). Therefore, although in FIG. 3, regions 131 and 132 are illustrated as being portions of a single wafer (e.g. obtained after step 115 of the prior art as described above), a comparison can be made across wafers to determine if the two signals diverge from each other (to implement act 124 of FIG. 2).

Figure 3:
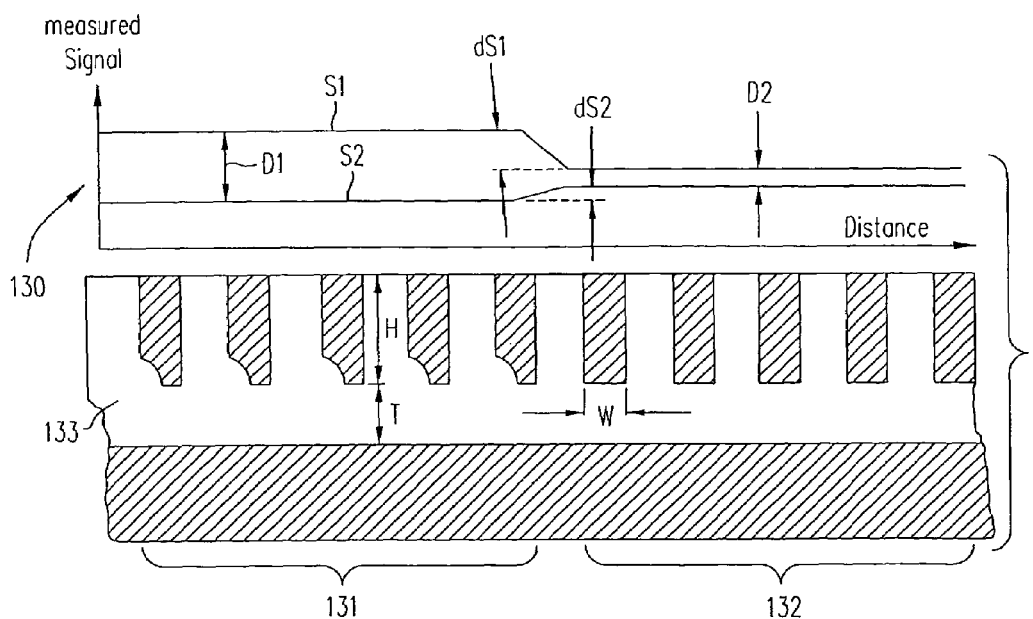
FIG. 3 illustrates, in a graph 130 shown relative to a structure 115, the measurements S1 and S2 in the presence and absence of voids.
Figure 4:
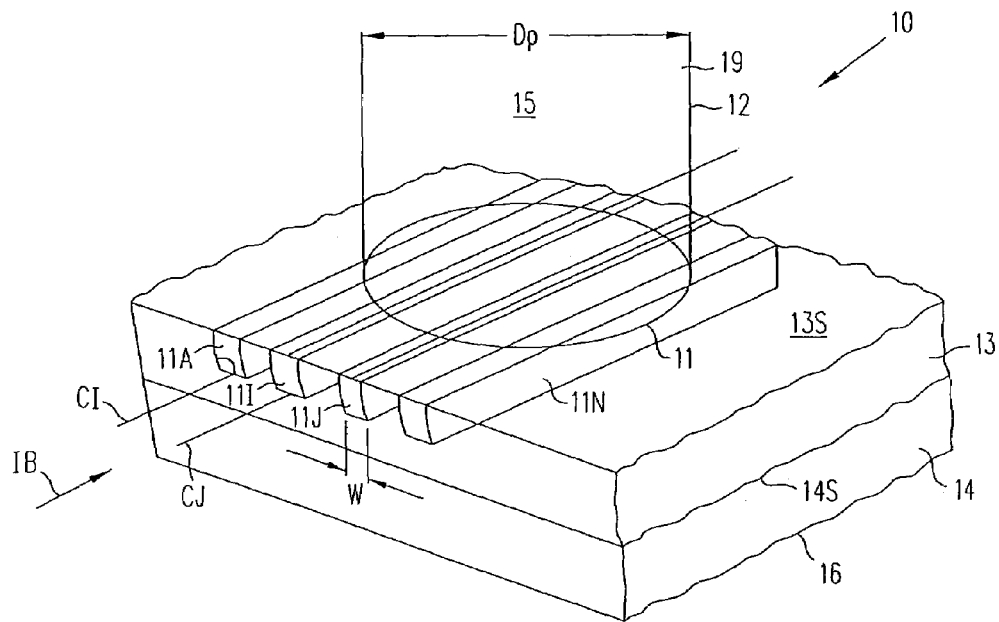
FIG. 4 illustrates, in a perspective view, a portion of a structure having a number of traces in a region illuminated by a beam of electromagnetic radiation in accordance with the invention.

In an alternative embodiment, a relative comparison is made between divergence D1 at one location as compared to divergence D2 at another location (both locations being in the same structure) as illustrated in FIG. 3. In one example of the just-described alternative embodiment, voids are deemed to be present if separation D1 at the current location is at least a predetermined percentage (e.g. 50% or 1000%) of the separation D2 in another location (e.g. a location that does not have one of the two layers in which case the predetermined percentage may be 50% for example, or a location that does not have a void in which case the predetermined percentage may be 1000% for example).

Acts 122 and 123 can be performed contemporaneously (e.g., just before, during or just after each other). Moreover, acts 122–124 can be performed in-situ during wafer fabrication (see method 120), immediately after creation of a region (see act 121; e.g. after chemical mechanical polishing), so as to adjust the fabrication process (see act 125) and discard the wafer if voids are determined to be present. The process being adjusted in act 125 can be, e.g. a sidewall deposition process or a fill (plating) process, or both. The specific adjustment to be made depends on the process, and knowledge of which parts of the process are most susceptible to change, and which parts have the strongest effect. If no voids are found, fabrication is continued with the wafer. Depending on the embodiment, the just-described measurements may be performed repeatedly (either before or after act 124), so that a number of regions (which may be, for example, an integral multiple of the number of dice) of a wafer are evaluated before the wafer is processed further (which further processing may be performed in the normal manner).

Figure 2:
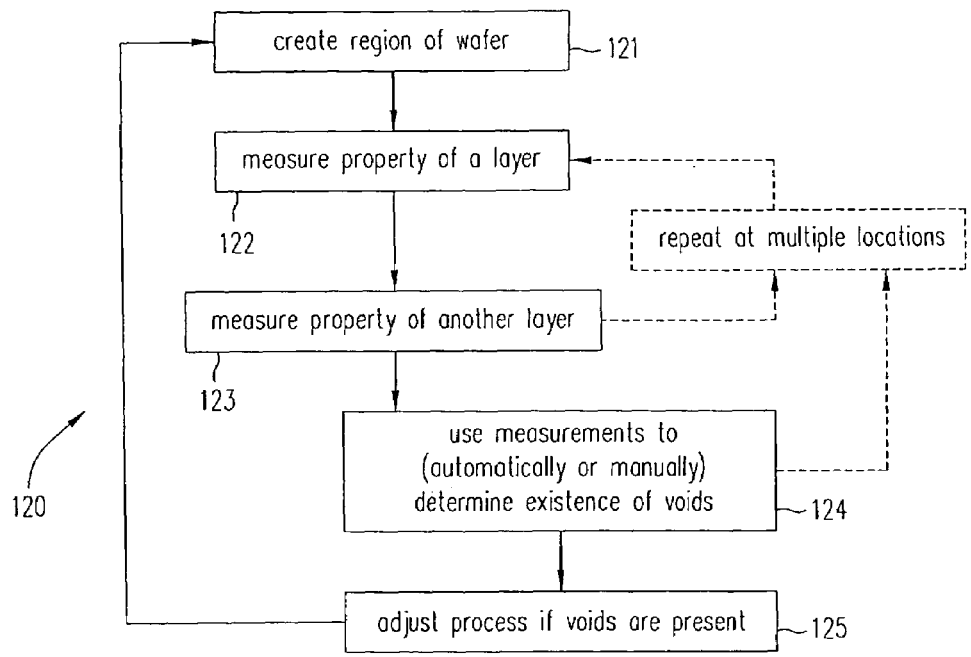
FIG. 2 illustrates, in a flow chart, a method for detecting voids in accordance with the invention.

Act 124 in FIG. 2 may be implemented by performing actions other than comparison. For example, in other embodiments, measurements from the two acts 122 and 123 are used in a formula (which can be, for example, simple multiplication) and the result is used to detect voids (e.g. by comparison against a threshold which may be determined from "reference" structures). Moreover, in one embodiment, the amount of adjustment made in Act 125 depends on the magnitude of divergence D. Specifically, the amplitude of separation of the two signals may be used as a measure of the size of the voids.

Depending on the embodiment and on the materials used in a wafer, the above-described change dS2 in signal S2 can be negligible (i.e. not noticeable), as compared to the change dS1 in signal S1. For this reason, one embodiment monitors a change in signal S1 alone instead of looking for changes in both signals S1 and S2. One variant of this embodiment does look at signal S2 but only after finding a change in signal S1, and then only as a confirmation, before determining that voids exist at this location. Instead of looking for confirmation by a change in S2, such an embodiment may use some other indication, e.g. a corresponding change in a global property (as opposed to a local property) may be used to rule out voids as the cause for the change in S1. Detecting a divergence in two signals (e.g. S1 and S2) at the same position reduces (and even eliminates in one example) the possibility of falsely determining that voids are present. Such a false measurement may be obtained when monitoring only one signal, e.g. by a scratch on the surface that changes both the dielectric and metal thickness.

Moreover, depending on the type of properties being measured and the material in the two layers, one or both of the measured signals may be scaled and aligned to one another. Also depending on the embodiment, any properties (also called "dimensional properties") of the two layers that depend on the dimensions of the features in the wafer may be measured (in acts 122 and 123 of FIG. 2) by any method well known in the art. Note, however, that one or more non-dimensional properties (such as conductivity and adhesion of metal to the dielectric) are measured in alternative embodiments.

In one embodiment, a signal indicative of the thickness of a dielectric layer of a damascene structure is measured and another signal indicative of the thickness (or cross-sectional area) of the traces supported by the dielectric layer is also measured. In another embodiment, a resistance measurement measures the line cross-section, and a dielectric measurement measures the thickness of the structure. Comparison of these two measurements determines whether a change in resistance is due to thickness variation or line width variation—in the former case the cause may be polishing, in the latter it is a lithography problem.

Instead of the just-described dimensional properties, other properties of the materials in the wafer can be measured (in acts 122 and 123). For example, in one embodiment, the average resistance per unit length of the traces is measured (in any manner well known in the art). Note that in the just-described example, the measured resistance can be converted into cross-sectional area if the composition of the conductive material used to form the traces is known. In another example, the thermal conductivity of the insulator between the lines is measured. Here again the resistance signal is a function of thermal conductivity between the lines. The resistance per unit length can be measured using a thermal method such as described in U.S. Pat. No. 6,054,868, but as the thickness of the lines tracks the dielectric thickness, so variations in thermal conductivity (or for that matter, adhesion of the lines to the dielectric) could be measured in a similar manner.

Acts 122 and 123 can be performed in any manner well known in the art for measuring such properties. One method of measuring resistance per unit length is physical probing of lines. Usually this is done with a serpentine structure with bond pads at each end. The length of the line is known, and the probed resistance divided by the length gives the resistance per unit length. One way of measuring cross-section is to physically cut and image the line. A common method is the FIB-SEM described earlier, where a focused ion beam (FIB) is used to mill away a cut into the line and then a scanning electron microscope (SEM) is used to image the cross-section. The thickness of a dielectric layer is easily measured using a number of methods, such as measuring reflection vs. wavelength (reflectometry) or ellipsometry. Moreover, the polarization methods described in International Publication No. WO 01/67071 A2 may be used with patterned lines.

In a first embodiment, act 122 is implemented as follows: a single beam is used as described in International Publication No. WO 01/67071 A2 to measure the thickness (e.g. T+H in FIG. 3) of dielectric layer 133, by measuring electromagnetic radiation reflected by the structure and polarized perpendicular to the traces. In this embodiment, act 123 may be implemented, to measure the average thickness (or cross-sectional area) of traces in contact with the dielectric layer, in any manner well known in the art (including the above-described prior art methods).

In a second embodiment, act 123 is implemented as follows: two beams are used as described in U.S. Pat. No. 6,054,868 wherein electromagnetic radiation in at least one beam (and preferably both beams) is polarized parallel to the traces. Depending on the implementation, the two beams may or may not be coincident. In the just-described second embodiment, act 122 may be implemented, to measure the thickness of the dielectric layer, in any manner well known in the art (including the above-described prior art methods).

A third embodiment uses act 122 as implemented by the first embodiment and act 123 as implemented by the second embodiment. Depending on the implementation of the third embodiment, one beam may be used commonly in acts 122 and 123, and the additional beam of act 123 may be used to obtain a second measure of the thickness of the dielectric layer (wherein a first measure is obtained in act 122 as described above). Such a second measure may be used to eliminate ambiguity that arises from the sinusoidal nature of the dielectric thickness signal, as described below.

As described above, such measurements from acts 122 and 123 are used in each of the first, second and third embodiments, to evaluate the silicon wafer for voids. Note that although the description refers to a wafer of silicon, the description is equally applicable to any multi-layered structure, such as any substrate that supports a conductive layer, and examples of a substrate other than silicon wafer include a glass plate and a resin core.

In one implementation, in each of acts 122 and 123 a beam 12 (FIG. 4) illuminates a multi-layered structure 10, and has a diameter Dp (at surface 13S of structure 10) that is selected to be several times larger than the width W of a trace 11I. For example, diameter Dp can be 2 microns and width W can be 0.15 microns (so that seven lines are simultaneously covered by beam 12). In this implementation, beam 12 merely illuminates region 11 and may or may not be focused on surface 13S (which is a surface of structure 10 exposed to a transmissive medium 15 such as air). In different embodiments, beam 12 is focused on (a) surface 13S, (b) surface 14S, (c) between surfaces 13S and 14S, (d) surface 16, or (3) above surface 13S. If a heating beam 19 is used as described elsewhere herein to evaluate a property of traces 11A–11N, both beams 12 and 19 are focused on the same surface (which can be any one of the just-described surfaces) in one embodiment. In another embodiment, beams 12 and 19 are focused on different surfaces.

In this embodiment, beam 12 is selected to have a wavelength greater than or equal to pitch p between two adjacent traces 11I and 11J. Beam 12 does not resolve individual features in region 11 (unlike a scanning microscope of the prior art which can resolve the individual features). Instead, beam 12 is used to obtain an average measure of one or more properties in illuminated region 11, e.g., of traces 11A–11N, or of layer 13 or a combination thereof. A single void in one of the traces under illumination causes the heat in that line to rise more than the others and contribute measurably to the signal. Therefore, the measurement can find isolated lines within the illuminated spot. The determination made in act 124 (FIG. 2) is an indication of the presence of voids in region 11 as a whole, rather than an indication that a void exists in a specific trace in structure 10.

Note that even a single line 11A may be under the beam 12, even if beam 12 has a diameter much greater than the width of line 11A, or even if the diameter of line 11A is comparable to the diameter of beam 12. In such a case, a single line 11A provides a signal for light in beam 12 polarized along the direction of line 11A in sufficient intensity to be measured, and a measurement for voids may be performed in an analogous manner. In addition, a beam 12 polarized orthogonal to line 11A will not be reflected by line 11A, and a dielectric thickness measurement may be made. Note that a measurement along the length of the line may also be made as discussed below in reference to FIGS. 16A–16D.

As noted elsewhere herein, such a structure 10 contains a number of traces 11A–11N (A≦I≦J≦N; N being the total number of traces) passing through a region 11 (also called illuminated region) of a layer 13. Traces 11A–11N (FIG. 4) are each substantially parallel to and adjacent to the other (e.g., centerlines CI and CJ of traces 11I and 11J that are adjacent to each other form an angle of less than 25° relative to one another). Traces 11A–11N have an index of refraction different from the index of refraction of layer 13, and therefore reflect the electromagnetic radiation in beam 12 that is directed at region 11. Note that traces 11A–11N need not be conductive, although in one embodiment the traces are conductive. Structure 10 can be (but is not required to be) a wafer of the type commonly used to manufacture integrated circuit dies.

A portion of beam 12 is reflected by region 11, and is used to generate an electrical signal (e.g., by use of a photosensitive element) that indicates an attribute (e.g., intensity or optical phase) of the reflected portion. The measured attribute in turn is used as an average measure of a property of a layer in region 11. For example, if the just-described acts 122 and 123 are performed in one region 11, a stage 24 (FIG. 12; described below) that supports structure 10 moves structure 10 so that a different region is illuminated, and then these acts 122 and 123 are repeated.

Two regions in which such measurements are made can be separated from each other, e.g., by distance which is same as the diameter Dp of beam 12. Alternatively, the two regions can touch each other or even overlap each other. When overlapping one another, the centers of the two regions may be separated by a small fraction of the diameter, e.g., by (1/10) Dp or less. Moreover, in this implementation, act 124 may be performed in one of two ways: (1) after acts 122 and 123 are performed, and before they are repeated; or (2) at the end, after acts 122 and 123 are performed repeatedly, for all regions of interest.

In an alternative embodiment, one beam polarized parallel to the lines is used for measuring a property of the lines (e.g. reflectance or conductivity) and one beam polarized perpendicular to the lines is used for measuring a property of the dielectric (e.g. adhesion to metal). In this alternative embodiment, the two beam measurements provide two inputs, giving more generalization to the measurement (as compared to use of unpolarized beams, for example). Also, one beam (such as a heating beam) could be a beam other than light, such as an electron beam and the other beam could be an optical beam, depending on the embodiment.

One embodiment involves stepwise movement ("hopping") from one region to another region of structure 10 when performing measurements of the type described herein. In the hopping process, stage 24 (FIG. 14) holds structure 10 stationary for a moment (e.g., 1 second) while a measurement is taken in one region, and then moves to another region (e.g., of the same structure). Another embodiment involves continuous movement (e.g. in a "sweep") of structure 10 relative to beam 12, while measurements of acts 122 and 123 are made simultaneously, and plotted in a graph as a function of distance (along the x axis) as illustrated in FIGS. 12 and 13 (described below). In some embodiments, measurements use hopping, but the hopping steps are on the order of the size of a spot formed by beam 12 on structure 10, so that the result when plotted as a function of distance is equivalent to a continuous movement sweep. Therefore, hopping in small steps on the order of or smaller than the spot size results in a scan equivalent to a sweep.

Figure 5:
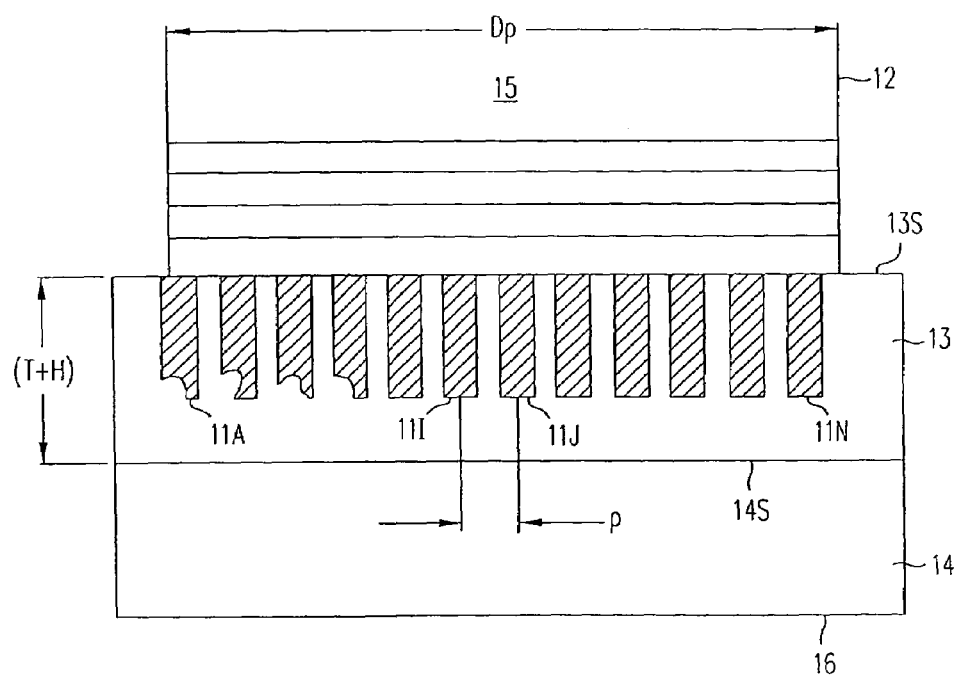
FIG. 5 illustrates, in an elevation view in the direction 1B of FIG. 4, the relationship between the diameter Dp of the beam and the pitch p between the traces.

Beam 12 can be linearly polarized, circularly polarized, elliptically polarized, nonpolarized or some combination thereof, depending on the implementation. So, in one implementation, beam 12 is nonpolarized, and one embodiment of act 122 (FIG. 2) generates a single electrical signal from the reflected portion. Such an electrical signal (as a whole) provides an average measure of the thickness (T+H) of a layer 13 (FIG. 5) that supports traces 11A–11N.

To implement act 122 (FIG. 2), another beam (also called "heating beam"), in addition to beam 12 (also called "probe beam"), can be used to heat traces 11A–11N (e.g., as described in the related patent, U.S. Pat. No. 6,054,868). In one embodiment the intensity of the heating beam (and therefore the temperature of traces 11A–11N) is modulated at a frequency that is sufficiently low to avoid creation of a thermal wave. If so modulated, a reflected portion of probe beam 12 is also modulated at the just-described frequency, in phase with the heating beam's modulation. So in this implementation of act 122 (FIG. 2), the reflected portion of probe beam 12 is measured by use of a lock-in amplifier.

A modulated component of the electrical signal (as measured by a lock-in amplifier) provides a measure of a property (such as thickness) of traces 11A–11N. The modulated component of the electrical signal, obtained from measuring the change in reflectance of traces 11A–11N, is sufficiently small relative to the overall electrical signal (due to reflectance of nonpolarized beam 12 by region 11) so that the overall electrical signal can be used (as noted above) as a measure of a property (e.g. thickness) of layer 13. Therefore, a measure of the modulated component in act 123, and of the overall electrical signal (or its steady component) in act 122 together identify the presence of voids in a structure, through comparison in act 124, and such measurements can be performed in a single operation.

Instead of the just-described nonpolarized probe beam 12, a circularly or elliptically polarized probe beam can also be used as described herein for a nonpolarized beam (except that separate calibration is required for an elliptically polarized beam; specifically, in the case of elliptically polarized light, the intensities in the two directions are different: for example, if the ratio of intensity in the two directions is 2:1 (parallel:perpendicular), then the parallel signal will be twice as strong for the same reflectivity, and reflection in the parallel direction must be divided by 2 to compare to the reflection in the perpendicular direction).

Figure 6:
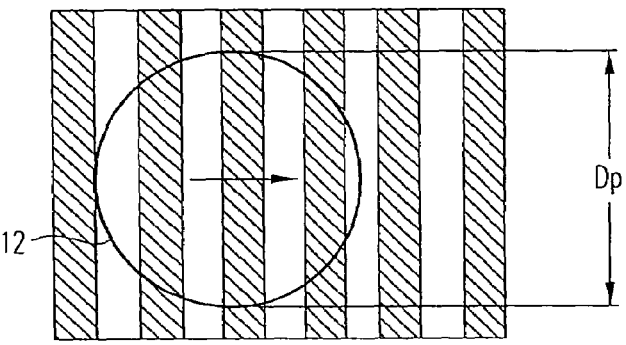
FIG. 6 illustrates the direction of polarization of the beam relative to the traces when respectively measuring a property of a dielectric layer underneath the traces.

In one embodiment, a reflected portion of a nonpolarized probe beam 12 is passed through a polarizer or a polarizing beam splitter to generate one or both components that have orthogonal polarization directions. For example, a polarizer may be used to select an individual polarization direction oriented perpendicular to traces 11A–11N as illustrated in FIG. 6, for measurement of a property of layer 13 in act 122. The polarizer can be a polarizing beam splitter available from Melles Griot of Irvine Calif. (see, for example part number 033 PBB 012).

When probe beam 12 (FIG. 6) is polarized perpendicular (i.e., θ=90°) to traces 11A–11N, then traces 11A–11N appear transparent to beam 12 due to the orientation, as long as the wavelength exceeds the pitch. So, probe-beam 12 has energy that passes through layer 13 (that is at least partially transmissive), and the remaining energy of probe beam 12 is reflected (e.g., by surface 14s; see FIG. 4) or absorbed. The transmitted portion passes between traces 11A–11N in the direction of incidence and also in the opposite direction (after reflection), because traces 11A–11N act as a polarizer, as described in, e.g., the Optics Handbook, pages 10–72 to 10–77.

For a given wavelength λ of probe beam 12, as the pitch p (FIG. 5) is reduced below λ (and the number of traces in region 11 is increased correspondingly) a parallel polarized beam is reflected more effectively and a perpendicular polarized beam is transmitted more effectively. Specifically, an extinction ratio increases with reduction of pitch. So, in one embodiment, wavelength greater than pitch is used to yield a large extinction ratio (e.g., greater than 2). When pitch is greater than or equal to 0.85 μm, the probe beam diameter Dp becomes on the order of the width of the traces, so that eventually there is no transmission of the incident light, and instead there is full reflection. For this reason, a larger probe beam diameter Dp may be used in such cases, so that a number of traces are illuminated.

Figure 7:
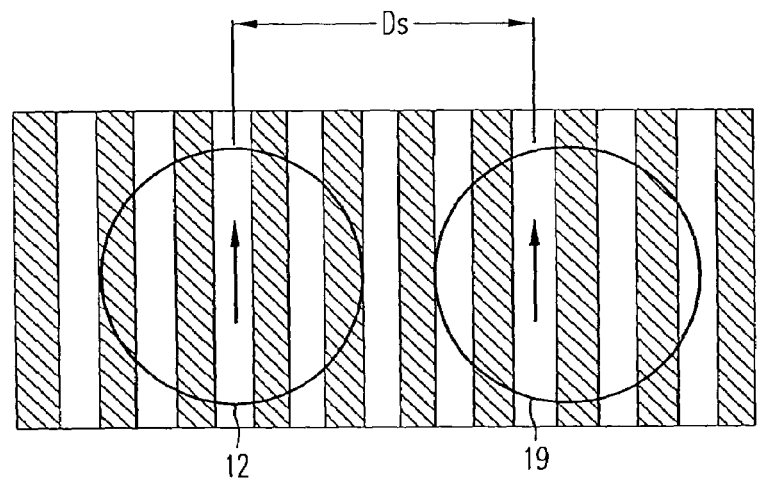
FIG. 7 illustrates the direction of a heating beam (used in one embodiment in addition to the beam of FIGS. 6 and 8) relative to the traces when measuring a property of the traces.

Thereafter, the polarizer may be rotated or replaced with another polarizer to select a polarization direction parallel to traces 11A–11N as illustrated by beam 12 in FIG. 7, for measurement of a property of traces 11A–11N in act 123. When polarized parallel to traces 11A–11N, a majority of the energy of beam 12 is reflected by traces 11A–11N, and the reflected portion is measured to determine a property of traces 11A–11N, e.g., reflectance.

The predetermined frequency of modulation of heating beam 19 is selected to be sufficiently small to cause a majority of the heat to transfer by diffusion from region 11. Under such diffusive heat transfer conditions, the temperature of traces 11A–11N is approximately equal to (e.g., within 90% of) the temperature of these same traces 11A–11N when heated by an unmodulated beam (i.e., a beam having constant power, equal to the instantaneous power of the modulated beam). For example, the modulation can be sinusoidal between 0 and 50 milliwatts, i.e., P=50 sin(2π ft), where f is the modulation frequency. In such an example, at the time when the modulated power has an instantaneous value of 25 mW, the temperature under heating beam 19 approximately equals (e.g., is no less than 90% of) the temperature obtained with a heating beam having constant power, e.g., 25 mW. In one example, heating beam 19 has a wavelength of 0.83 microns, has an average power of 10 milliwatts, a diameter of 2 microns and is modulated at 2000 Hertz.

In one embodiment, the modulation frequency is selected to cause all traces 11A–11N illuminated by heating beam 19 to be at substantially the same temperature relative to one another (e.g., varying less than 10% between adjacent traces). Such a linear response condition occurs when the thermal wavelength λ (which is the wavelength of a thermal wave that is formed in the structure) is at least an order of magnitude larger than the diameter Dp of the illuminated region 11.

Therefore, when a heating beam 19 is modulated, the temperature T (and therefore the reflectance) of traces 11A–11M is also modulated in phase with modulation of the heating beam (under linear response conditions). Probe beam 12's reflected portion (which is sensed to generate an electrical signal) is also modulated, in phase with modulation of heating beam 19. The modulated electrical signal is detected by use of a lock-in amplifier as stated in U.S. Pat. No. 6,054,868. The modulated electrical signal can be used to identify variations in one or more materials of the traces (e.g., resistance per unit length which is indicative of cross-sectional area).

Figure 8:
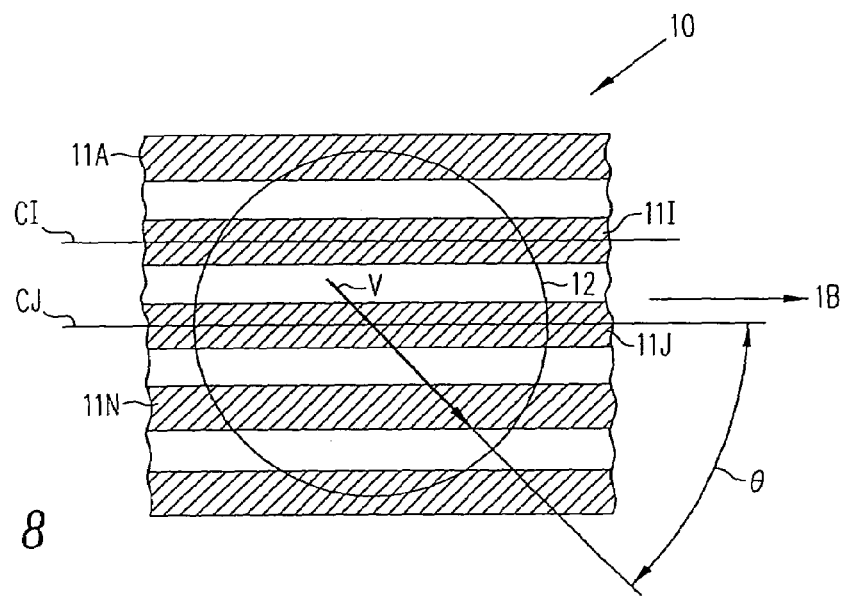
FIG. 8 illustrates a beam having a parallel polarized component and a perpendicular polarized component for use in measuring properties of the traces and of the dielectric layer contemporaneously.

In an alternative embodiment, probe beam 12 is unpolarized, and a polarizing beam splitter separates unpolarized light reflected by traces 11A–11N into two orthogonal polarization components, for instance, aligned parallel and perpendicular to traces 11A–11N. The parallel and perpendicular polarized components are then intercepted by separate photodetectors to simultaneously measure their individual intensities. Moreover, a polarized probe beam 12 can be used in several ways, including, e.g., orienting beam 12 (FIG. 8) so that the electric field vector v thereof is at a predetermined angle θ (such as 0°, 90° or 45°) relative to the longitudinal direction 1B (FIG. 4) of traces 11A–11N.

Figures 9, 11:
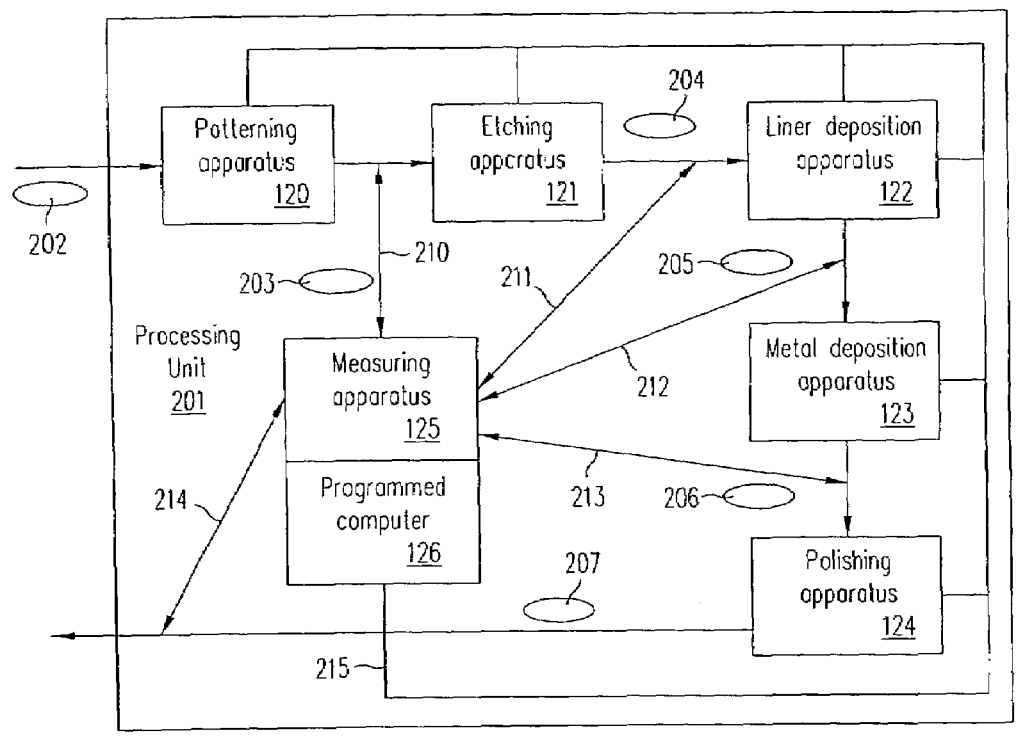
FIG. 9 illustrates, in a block diagram, use of the measurement apparatus of FIG. 12 in a processing unit for fabrication of semiconductor wafers.
FIG. 11 illustrates a two dimensional map of a wafer showing dies that have different voiding.

In one embodiment, a damascene structure is formed in a wafer by a processing unit 201 that includes measuring apparatus 125 (FIG. 9) to evaluate the wafer for voids. Specifically, a patterning apparatus 120 deposits and exposes a photoresist layer and an etching apparatus 121 exposes and develops the photoresist layer 101 (FIG. 1) to form grooves in dielectric layer 102 on wafer 203 (FIG. 9). Thereafter, an etching apparatus 121 etches through the patterned photoresist layer to form grooves in an underlying insulation layer thereby to form wafer 204 (FIG. 9). Next, a liner deposition apparatus 122 forms a barrier layer in the etched grooves and a conductive material 106 (FIG. 1) is blanket deposited on wafer 205, by a deposition apparatus 123 thereby to form substrate 206. Next a polishing apparatus 124 is used to polish back layer 106.

Figure 10:
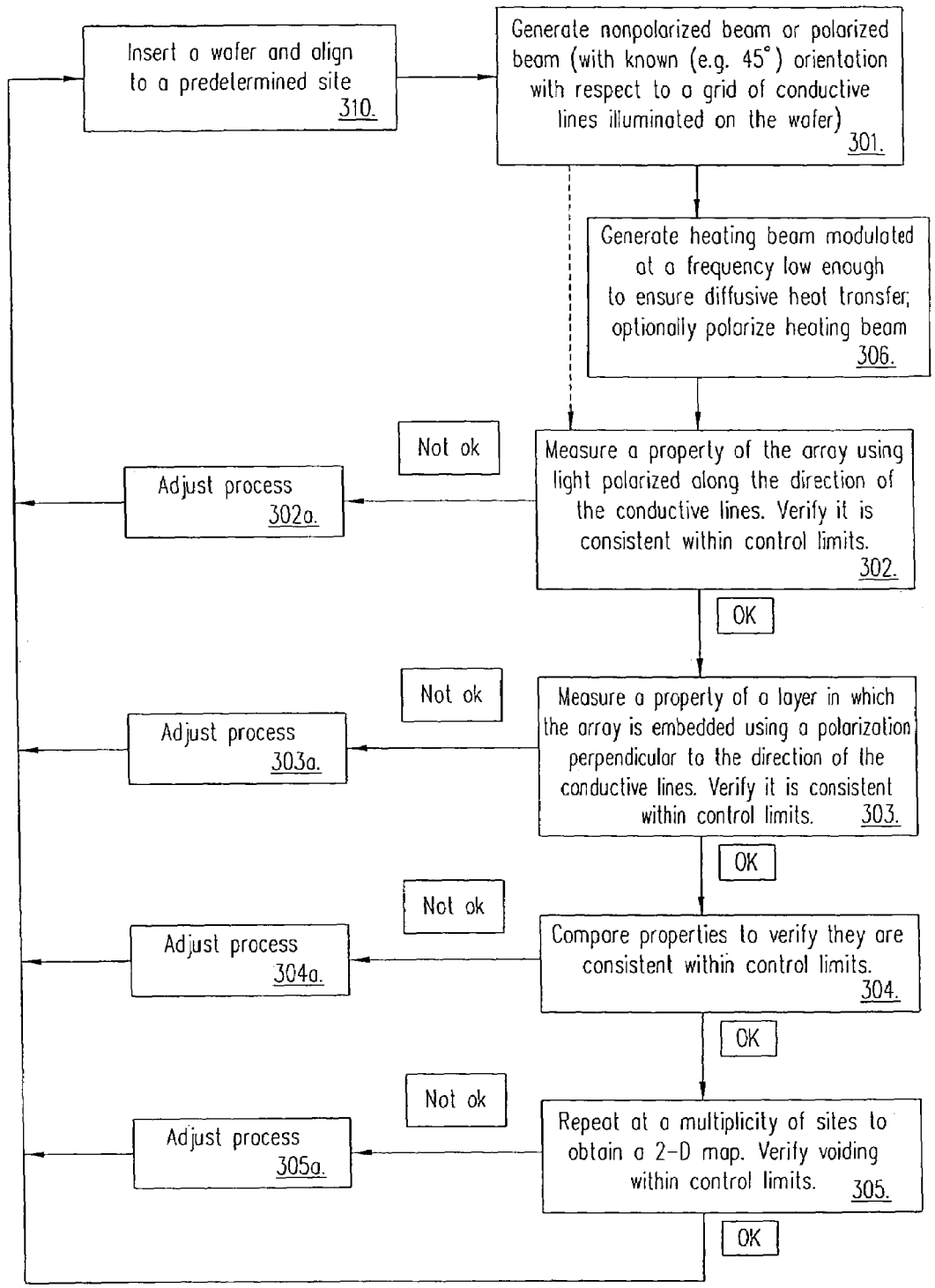
FIG. 10 illustrates, in a flow chart, one embodiment that implements the method of FIG. 2.

Thereafter, a measuring apparatus 125 in processing unit 201 is used with a programmed computer 126 to perform a process 300 illustrated in FIG. 10. Process 300 may also be performed at other times, depending on the embodiment, e.g. as illustrated by arrows 210–213. At the conclusion of process 300, programmed computer 126 supplies a process parameter (used in the fabrication process) on a bus 215 that is coupled to each of apparatuses 120–124 described above. A change in the process parameter can be determined automatically by software in programmed computer 126 (e.g. by performing a table look up), or can be entered by a human operator. Note that in one embodiment a single measurement operation on wafer 207 detects the presence of voids, so that multiple measurement operations are not required. Note that at any point during wafer fabrication of the type described above, a wafer can be subjected to the measurement process 300.

In act 310 of process 300 (FIG. 10), a wafer is inserted into a wafer aligner (in measuring apparatus 125 of FIG. 9), and traces formed therein are oriented in a predetermined direction relative to a stage. Next, in act 301, a probe beam 12 that is either unpolarized or polarized at a known orientation relative to the predetermined direction (i.e., relative to the traces) is generated, and illuminates the traces. Next, in act 306, a heating beam 19 that is modulated at the above-described predetermined frequency is generated, and also illuminates the traces. Heating beam 19 may or may not be polarized (and if polarized, the orientation is parallel to the traces). Thereafter, in act 302, resistance per unit length (or thickness) of the array of traces is measured, by sensing electromagnetic radiation that is reflected by the traces, that is polarized parallel to the traces, and that is modulated at the predetermined frequency. A programmed computer 126 (FIG. 9) checks if the measured property is within a predetermined range, and if not a process parameter is adjusted (e.g., via bus 115 illustrated in FIG. 9) as illustrated by act 302a.

Then, in act 303, a property of the layer 13 in which the array of traces is embedded is measured, using a beam polarized perpendicular to the traces. Computer 126 checks (in act 303) if the measured property is within a predetermined range, and if not another process parameter (or even the same process parameter described above) is adjusted, as illustrated by act 303a. Next, computer 126 compares (in act 304) the two measurements to one another, and if there is a large deviation indicating the presence of voids, yet another process parameter (or even the same parameter) is adjusted, as illustrated by act 304a. Then the above-described acts are repeated (in act 305) at a number of sites.

Although in the above paragraph a comparison between two different measurements has been described in reference to act 304, the same measurement may be compared (i.e. to itself) to identify a defect. Specifically, a void may be detected by scanning a region to find a signal in excess of a base line, e.g. wherein a peak in the measured signal represents a void, and such peaks may be identified as local maxima in a measured signal (regardless of the properties of the underlying oxide and the related signal from the underlying oxide). Therefore instead of comparing two signals from the same location, the same signal from different locations is compared in such an embodiment.

Note that the measurements can also be displayed to an operator (by computer 126) in a two-dimensional map of the wafer as illustrated in FIG. 11. For example, dies 5, 9, 11 and 12 may be shown highlighted (e.g., brightened, darkened or different color or hatched) to indicate the presence of voids (if computer 126 is programmed to detect voids). There may be different types of highlighting (e.g., die 5 v/s dies 9, 11, 12) to show the degree of variation in the presence of voids. Also, instead of highlighting, other mechanisms can be used, to convey the same information, e.g. dies 9, 11 and 12 may be shown connected by a contour line (or shown shaded in a common color), to indicate the presence of a certain percentage of voids, while die 5 may be connected to other dice that contain the same percentage of voids, by another contour line (or color). Instead of using computer 126 to determine the presence of voids, the measurement separations D in all dies may be displayed (in correspondingly varying shades of gray or color).

Such two-dimensional maps indicate variations across the production wafer (e.g., dies 5, 9, 11 and 12) are located at the periphery of the wafer and therefore indicate a problem at the periphery. An example of such a problem could occur due to voids forming in the metal traces, typically if dies all around the periphery fall outside of a control limit (in the example dies 13–26 may fall with the control limit and so a different problem may be present). If several dies of a particular region (e.g., dies 5, 9, 11 and 12 in the bottom right corner) are affected, there may be a problem in that region, such as a number of voids in one or more of the traces in the illuminated region.

Figure 12A:
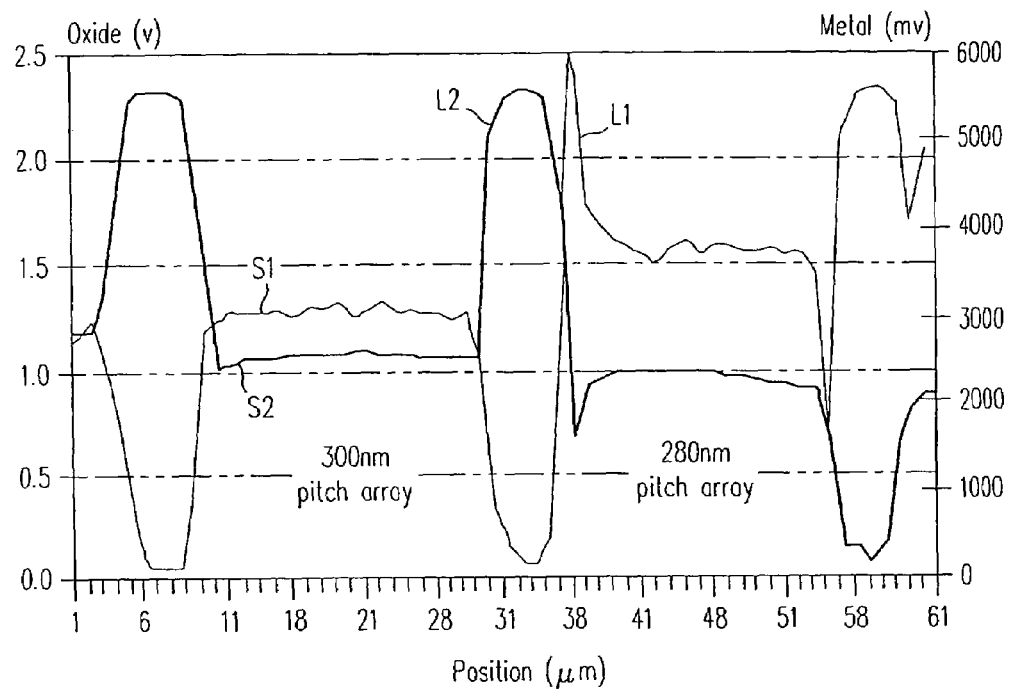
FIGS. 12A and 12B illustrate, in graphs, plots of measurements performed in the embodiment illustrated in FIG. 10.
Figure 12B:
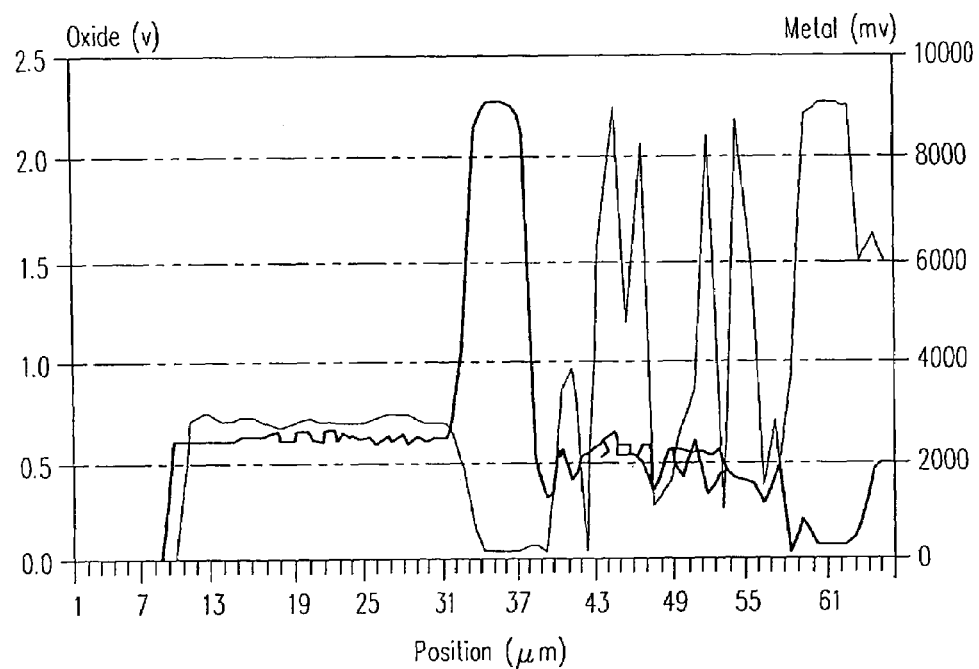

Instead of or in addition to the two-dimensional map of the wafer illustrated in FIG. 11, the two measurements in each die can be displayed to an operator in the form of graphs as illustrated in FIGS. 12A and 12B. Such graphs may be displayed instantaneously, as the measurements are being made. Alternatively the graphs may be displayed in response to a query from an operator, e.g. after the two-dimensional map is displayed. FIG. 12A illustrates a scan across 0.14 µm wide lines that are formed in two arrays: a first array with pitch (line-to-line spacing) of 0.3 µm illustrated in the left half of FIG. 12A and a second array with pitch of 0.28 µm illustrated in the right half of FIG. 12A. The large signals L1 and L2 come from a region between the two arrays. Note that the dielectric thickness signal S1 changes in the same manner as the metal resistance signal S2. Note that there are no voids in both arrays illustrated in FIG. 12A.

The effect of voiding at a different site in the same wafer is illustrated in the right half of FIG. 12B (and there is no voiding in the left half). Note that in the right half of FIG. 12B, the metal resistance signal S2 spikes to very high values Sa–Sd consistent with high resistance, while the dielectric signal S1 shows far less variation. In such a case, the voiding is not within control limits, and a process parameter is adjusted, as illustrated by act 305*a*. If a production wafer has no voids, one or more additional layers are formed on the wafer by the various apparatuses 120–124 (FIG. 9), and then the wafer is returned to the aligner (in act 310), and the measurement and control acts 301–305 are repeated. Note that while forming the additional layers, acts 301–305 and 310 can be performed on a different production wafer.

Figure 13A:
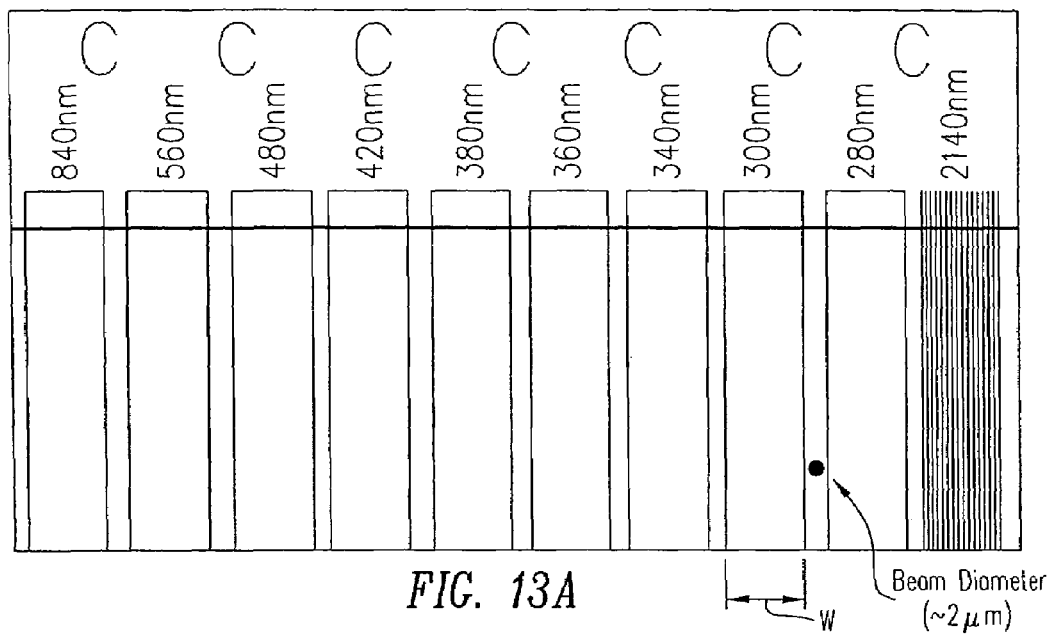
FIG. 13A illustrates, in a top down view through a microscope, a number of trench arrays in a reference wafer and the relative size of a laser beam used in a method of the type described herein.

FIG. 13A illustrates a wafer that was evaluated in the manner described herein. Specifically 0.12 µm trenches were patterned in 8 kA thermal oxide on silicon wafers. A 250 Angstroms PVD Ta barrier was deposited. Trench voids were intentionally created by sputtering very thin (250 Ång) copper seed in the trenches. Due to discontinuous Cu seed coverage at the bottom of some of the trenches, copper could not be electroplated at those locations, resulting in sidewall voids. After CMP and anneal, wafers were evaluated to determine if method 300 (FIG. 10) could detect copper voids.

Method 300 was used to scan two adjacent trench arrays, (labeled 300 nm and 280 nm) each of which had 0.14 µm target trench widths. The pitch of trenches and lines in the arrays measured is 280 nm and 300 nm as shown in FIG. 13A. Each array is about 20 µm wide, as shown by width W in FIG. 13A. The relative beam size of some tools is also shown in FIG. 13A to identify the spatial relationship between the beam size, the array width, and trench width. Apparatus 125 (FIG. 9) is capable of scanning across an array because of the relatively small diameter of the heating and probe beams. The beam spot may overlap from 5–10 trenches, depending on the geometry of the wafer. As noted elsewhere, beams of spots that overlap only one trench or that overlap more than 10 trenches may also be used, depending on the embodiment.

Relatively speaking, small perturbations in the trenches are more easily detected with small beams, as compared to large beams. After evaluation by apparatus 125, a reference wafer is normally evaluated by a conventional apparatus such as a scanning electron microscope (SEM). SEM photos 1701–1704 shown in FIG. 13B are representative of voids discovered in the measurement areas.

Figure 13B:
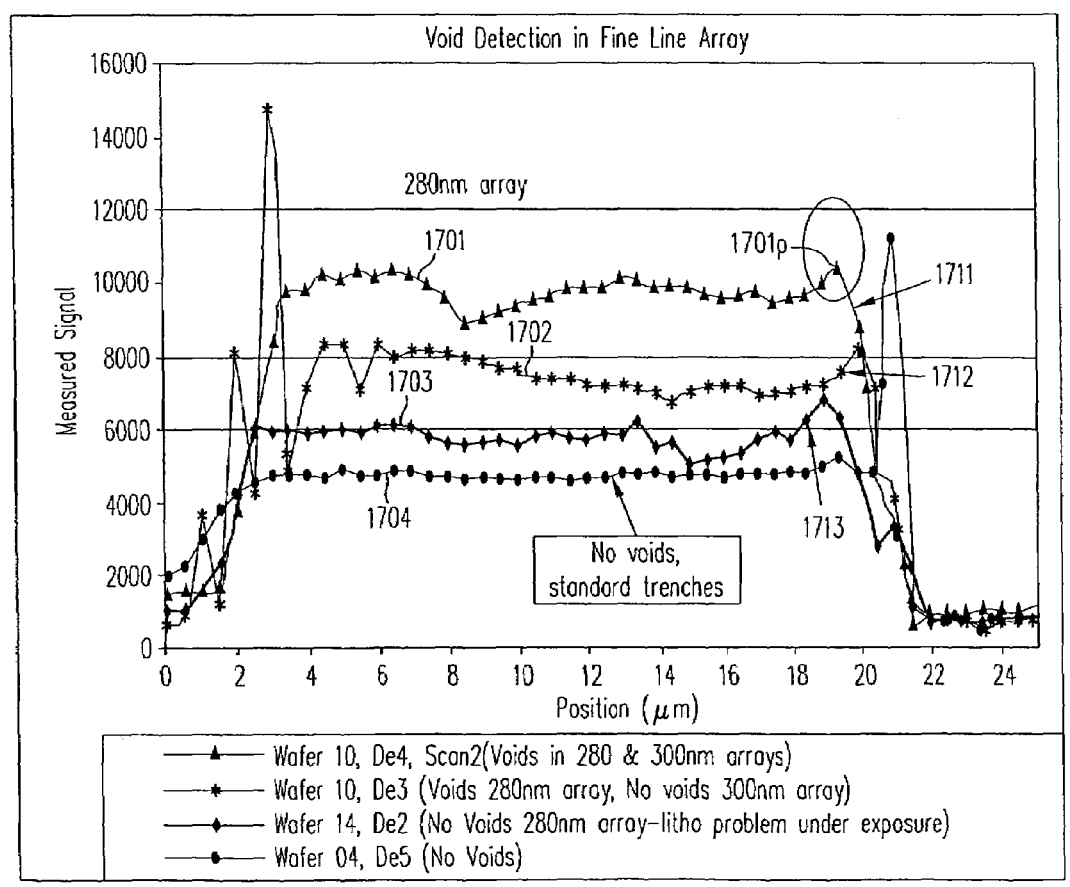
FIG. 13B illustrates, in a graph, correlation of a measured signal to the presence or absence of voids.
Figures 1, 13B:
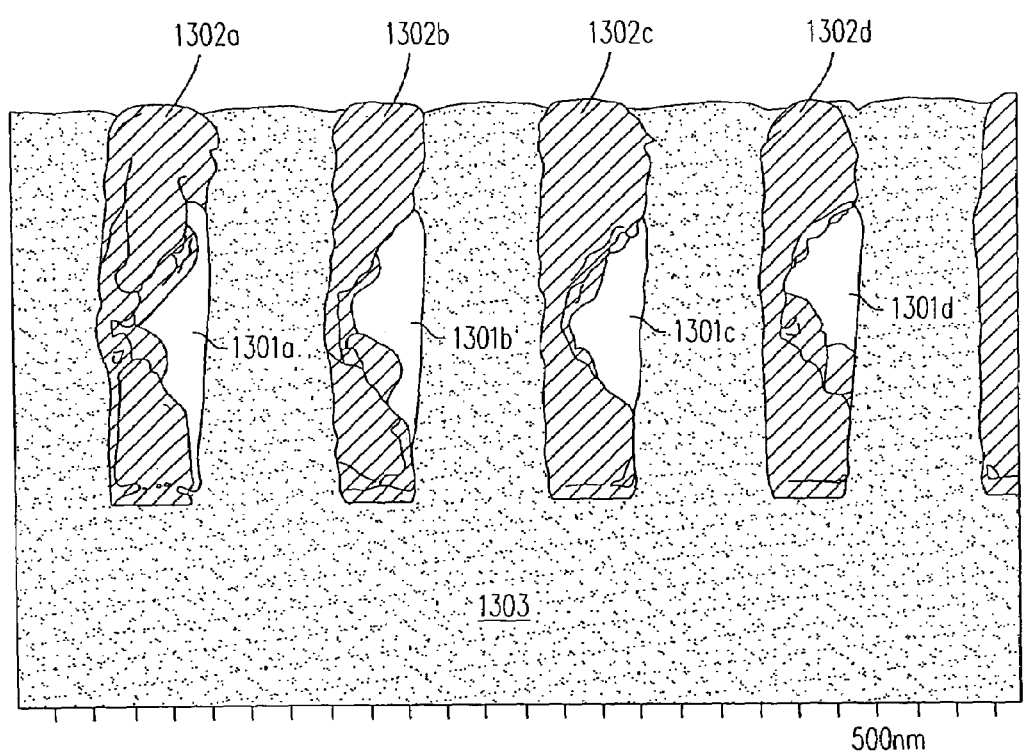
Figures 2, 13B:
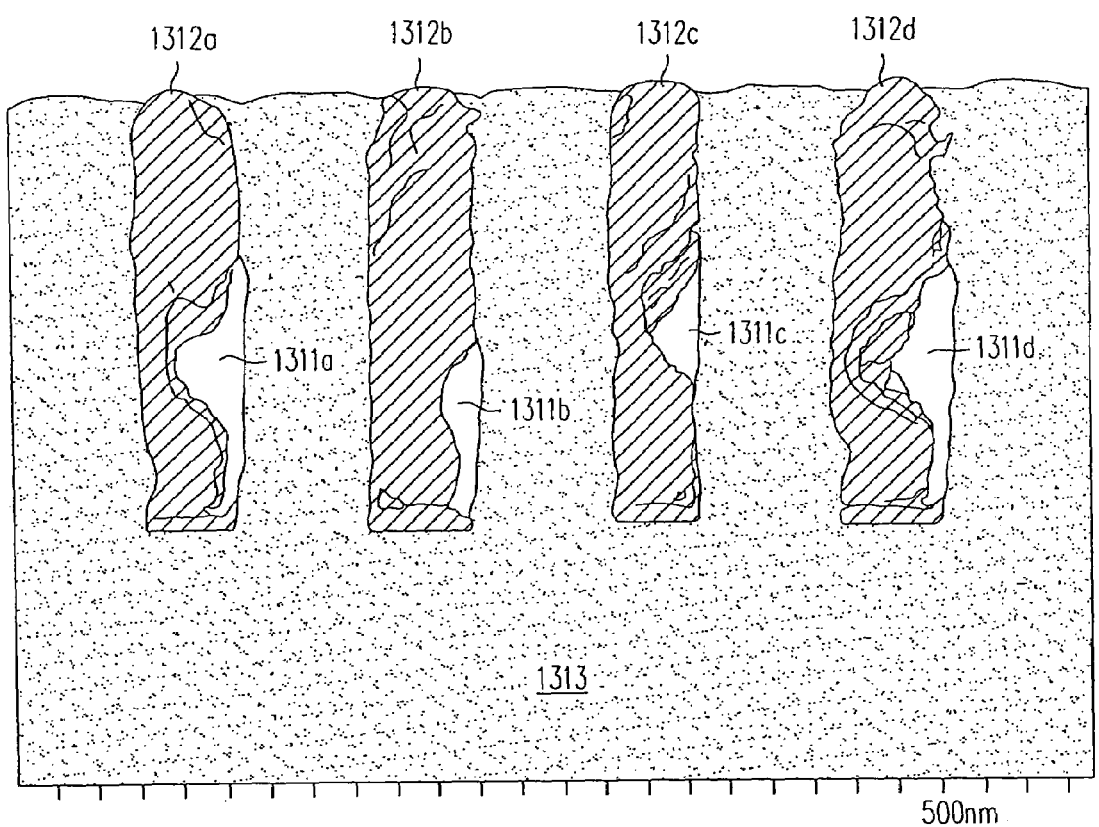
Figures 3, 13B:
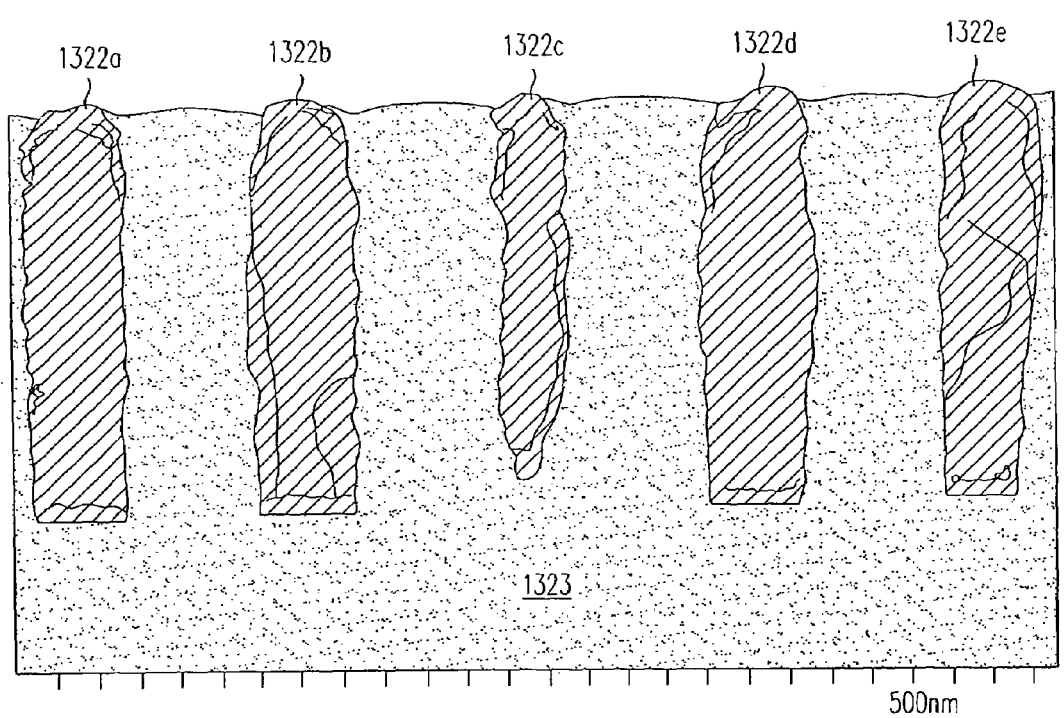

Results from four different samples measured by apparatus 125 are shown in a graph illustrated in FIG. 13B. Each of the four lines 1701–1704 represents a different trench array. Each of lines 1701–1704 is a curve that fits 1 µm interval individual measurements across one 20 µm wide, 280 nm pitch array. The x-axis shows the measurement position, in microns. The y-axis represents the relative thermal/electrical resistance of the copper. A lower magnitude signal implies a larger cross-sectional copper area. The curve 1704 labeled "No voids, standard trenches" shows uniform and relatively low resistance across the trench array, implying that there are no voids or other defects that decrease the effective cross-sectional area of copper.

Trench voids and patterning defects result in higher base lines for the curves 1701–1703 which are for the corresponding structures in the cross-sections 1711 (Large Voids), 1712 (Medium Voids), and 1713 (No Voids Litho). The increased signal magnitude for these curves 1701–1703 suggests a smaller cross-sectional copper area, thus higher resistance. These curves 1701–1703 also indicate non-uniformity across the array, or variation in cross-sectional copper area from trench to trench. Cross-section FIB-SEMs 1711–1713 reveal voids and/or patterning defects in the areas measured on these samples, both of which account for higher and non-uniform line resistance.

Figure 13C:
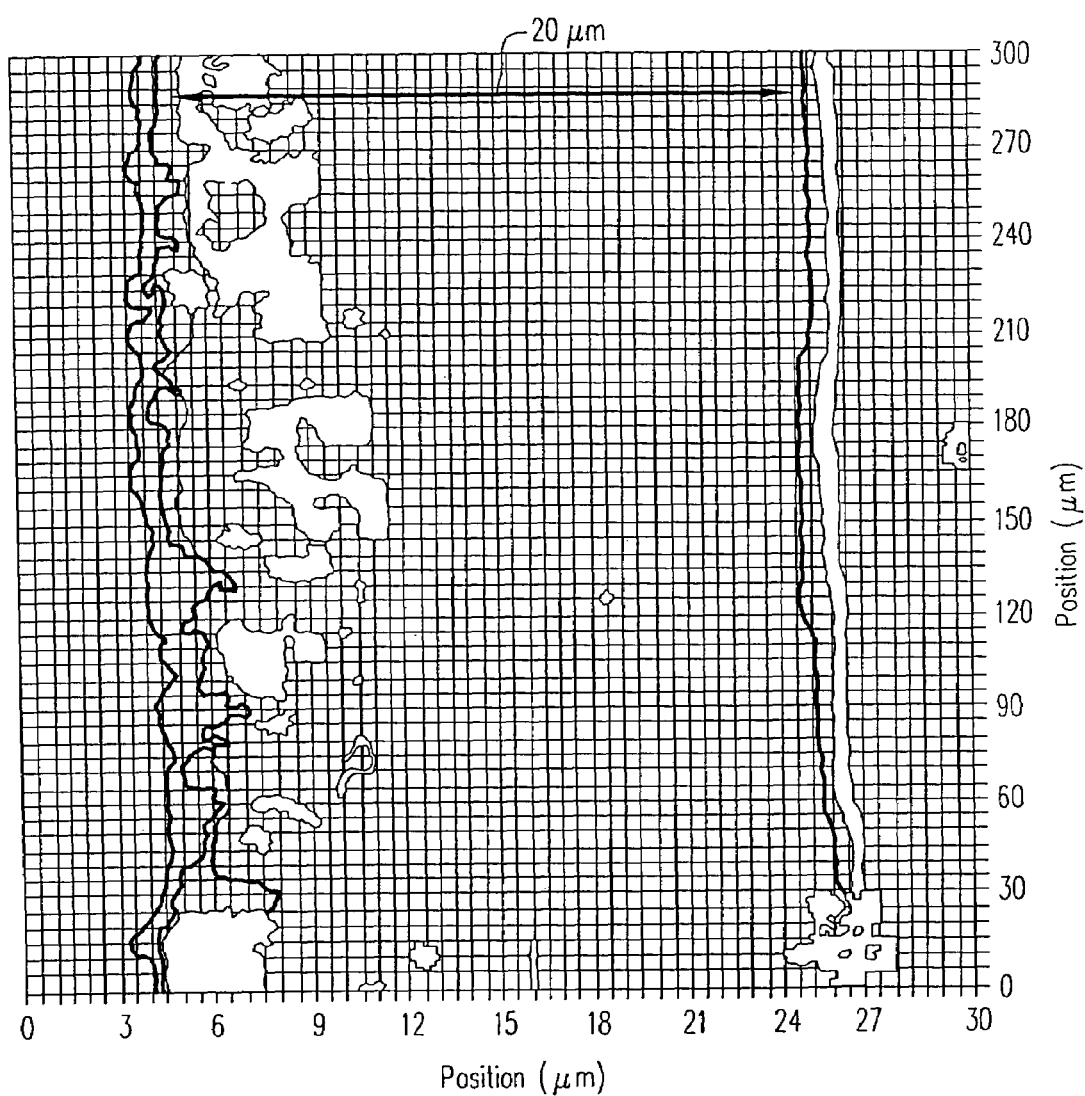
FIGS. 13C and 13D illustrate in a two dimensional graph and a three dimensional graph respectively, an area scan obtained by a method of the type described herein.
Figure 13D:
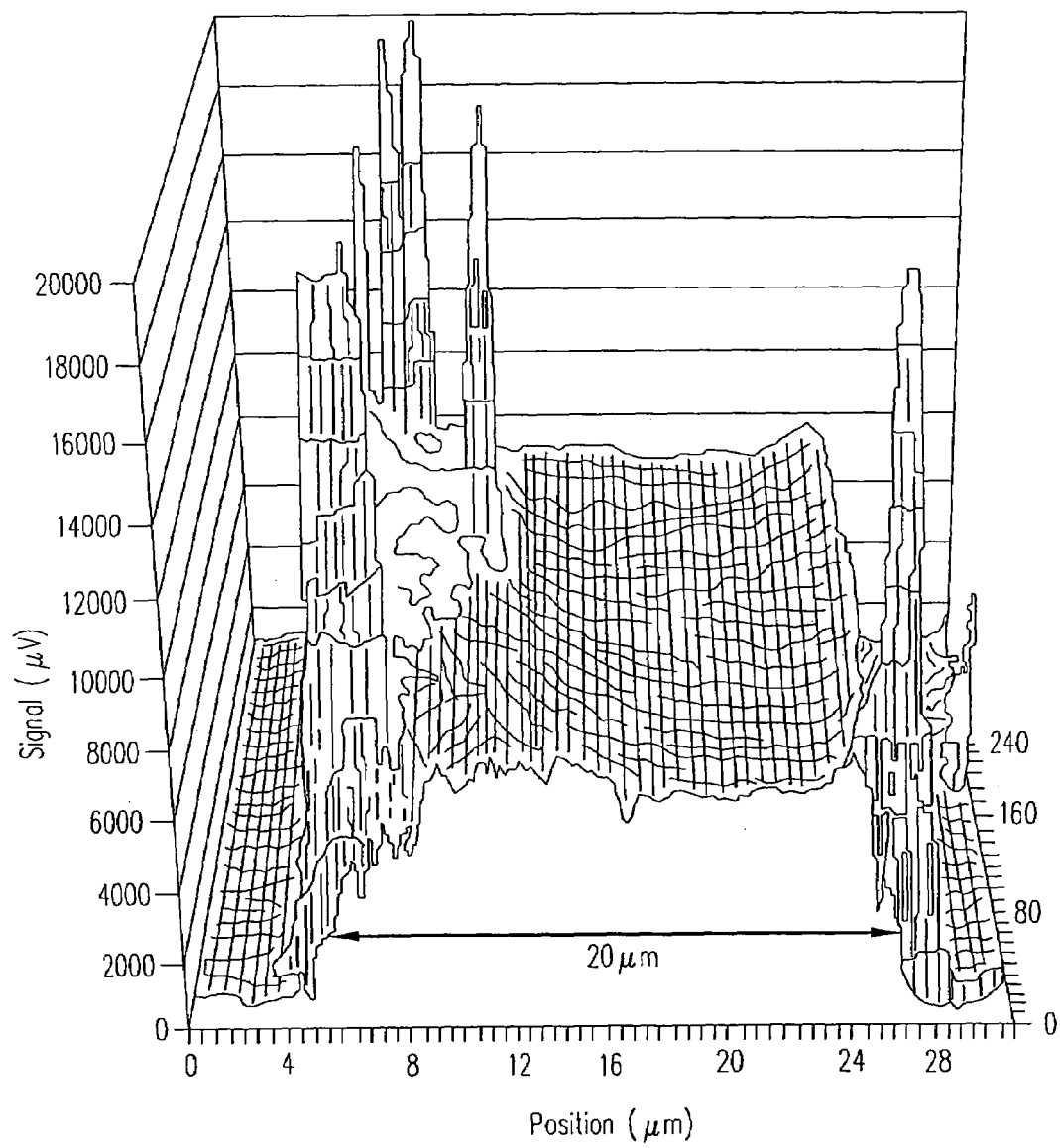

In one embodiment, a number of line scans are performed along the corresponding number of lines that are parallel to one another, thereby to obtain an area map of the Damascene structure under evaluation. In the example illustrated in FIGS. 13C and 13D, area maps are of a voided array of 280 nm lines which shows large peaks on the edge on the left side (e.g. between 6 µm–11 µm on the horizontal scale) of these graphs (both FIGS. 13C and 13D show the same information) due to the presents of large voids. Note that an erosion pattern across the array is also evident in FIG. 13C. In FIG. 13C, the different shades of gray indicate different amounts of voiding. The amounts of voiding for an area map may alternatively be shown in a three dimensional graph as illustrated in FIG. 3D. Note that instead of gray scales, contour maps, or color graphs can also be used, depending on the implementation.

Acts 301–306 of method 300 can be performed by use of a void measurement apparatus 125 (FIG. 14) having two lasers 331 and 335 that create two beams 301 and 302. Specifically, apparatus 125 includes a laser 331 for creating a beam 301 of electromagnetic radiation at a predetermined wavelength, such as infrared light, or ultraviolet light. Alternately, a source of X-rays, gamma rays, or radiation in the microwave or radio frequencies can be used. In one embodiment, laser 331 is a AlGaAs diode laser that emits electromagnetic radiation of wavelength 830 nm. Moreover the electromagnetic radiation emitted by laser 331 is linearly polarized in this particular embodiment.

The electromagnetic radiation created by laser 331 is transmitted through an optical fiber 332 to a collimator 333 that emits heating beam 301. In one implementation, heating beam 301 has a maximum power of, for example, 100 milliwatts. Apparatus 125 also includes lenses 304A and 304B that adjust the size of beam 101 to fill the aperture of an objective lens 315 also included in apparatus 125.

Apparatus 125 further includes a second laser 335 that creates a beam 302 of electromagnetic radiation used to measure a change in reflectance of traces 11A–11N in response to change in power of heating beam 301. In one implementation, laser 335 is an InGaAs diode laser that emits electromagnetic radiation of wavelength 980 nm. The electromagnetic radiation created by laser 335 is transferred by an optical fiber 336 to another collimator 307 also included in apparatus 125. Collimator 307 emits probe beam 302 having a maximum power of, for example, 7 milliwatts. Therefore, probe beam 302 has a power that is an order of magnitude smaller than the power of heating beam 301, so that conductive traces 11A–11N are not noticeably heated by probe beam 302. Moreover, collimator 307 emits electromagnetic radiation that is circularly polarized, so that beam 302 has components polarized in the parallel and perpendicular directions relative to traces 11A–11N.

Apparatus 125 also includes lenses 308A and 308B that adjust the size of probe beam 302 to fill the aperture of objective lens 315 (described above). Apparatus 125 also includes a dichroic beam splitter 310 that combines heating beam 301 and probe beam 302 to form a combined beam 311. Combined beam 311 passes through beam splitters 312 and 314 that are also included in apparatus 125, to an objective lens 315. Objective lens 315 can be, for example, a 0.9 NA, 100× objective lens available from Nikon of Yokohama, Japan.

A portion of combined beam 311 is deflected to a photodetector 313, such as part number J16-8SP-RO5m-HS from EG&G Judson of Montgomeryville, Pa., USA. Photodetector 313 is used to verify the alignment of combined beam 311 with respect to wafer 305, and to measure the incident power of one or both of beams 301 and 302. Apparatus 125 also includes a beam splitter 314 that diverts 10% of combined beam 311 to a focusing lens 317 and a camera 318. Camera 318 is used to observe beams 301 and 302 (FIG. 1B) on wafer 305, in order to focus combined beam 311 (FIG. 3) within region 111R (FIG. 1B) on wafer 305.

Light reflected from wafer 305 passes back through objective lens 315 and through beam splitter 312. Beam splitter 312 sends 50% of the reflected light through a filter 319. Filter 319 is a narrow band filter that removes the reflected portion of heating beam 303 while passing the reflected portion of probe beam 309. Thereafter, a polarizing beam splitter 338 passes one polarization component to detector 340 and deflects the other polarization component to detector 339. Detectors 339 and 340 simultaneously provide measurements, of the metal property and the dielectric property.

A signal from detector 340 (of the metal property) is amplified by a transimpedance amplifier 324 and a voltage amplifier 323 that provides the amplified signal to a lock-in amplifier 322. Lock-in amplifier 322 includes an oscillator as a frequency source that is used to detect the power of the reflected portion of probe beam 302 modulated at the predetermined frequency. The frequency source in lock-in amplifier 322 also provides a frequency signal on a line 321M to a laser driver 321. Laser driver 321 uses the frequency signal on line 321M to drive laser 331 at the predetermined frequency that is sufficiently low to modulate the amplitude of heating beam 301 to ensure heat transfer by diffusion as described herein.

In one embodiment, filter 319 is mounted on an actuator 337 that can be operated to remove filter 319 from the path of the reflected portion of the heating beam towards the polarizing beam splitter 338. When so removed, the reflectance of the heating beam is also measured, to obtain a second measure of the thickness of the dielectric layer in wafer 305. The second measure is needed because the reflectance of the dielectric layer is periodic in the ratio of thickness to wavelength. Therefore, at certain thicknesses, the reflection signal at the wavelength (e.g. 980 nm) of the probe beam is at a maximum or minimum of the cosine, and the sensitivity to changes in thickness is small. In this case, the measurement of dielectric thickness is taken using reflection of the heating beam.

Alternatively, a variable wavelength light source, such as a white light source, and a monochrometer may be added into the path of the reflected electromagnetic radiation, and the reflectivity measured at multiple wavelengths. Such measurement removes any ambiguity that may occur through use of a single wavelength probe beam to measure dielectric thickness. Note that instead of laser 335 generating a circularly polarized beam 302, another laser that generates a linearly polarized beam can be used with a half wave plate that is mounted on an actuator to change the polarization direction. In such an embodiment, polarizing beam splitter 338 is not used, and instead the measurements of metal property and dielectric property are made sequentially.

Numerous modifications and adaptations of the above-described embodiments will become apparent to a person skilled in the art of using lasers to measure semiconductor properties. For example, in an alternative embodiment, instead of using a laser to generate heating beam 301 to change peak temperature Tp of traces 11A–11N, another heat source (such as an electron gun) is used to modulate the temperature. Use of electrons in beam 301 instead of photons allows the diameter of beam 301 to be made smaller than possible when using photons. However, use of electrons in beam 301 requires measurement apparatus to include a vacuum chamber to contain the electron source.

As noted above, the just-described regions can be inside a single structure or spread across multiple such structures (e.g., in a reference structure that has known material properties, and a production structure that is currently being fabricated and whose properties are yet to be determined, or even multiple production structures). Note that acts 121, 124 and 125 described above in reference to FIG. 2 are optional, and may or may not be performed, depending on the embodiment. For example, the generated electrical signals may be manually evaluated. Alternatively, such evaluations (manual or automatic) may be performed independent of the fabrication processes of the structures.

Moreover, the above-described method and apparatus can be used with traces 11A–11N of any metal (such as copper or aluminum) or any silicide (such as titanium, cobalt, or platinum), irrespective of whether or not the traces have been annealed. Furthermore, depending on the embodiment, the thickness of layer 13 is measured in one implementation of act 122 by illuminating traces 11A–11N with polarized white light, and measuring the color of the reflected light, e.g. with a camera (and optionally an image processor). Films (such as layer 13 in FIG. 4) that are sufficiently thin (e.g. about 1–2 μm thick) have a reflectance that is a function of wavelength, and therefore reflect light of a color that depends on the thickness (e.g. thickness T+H in FIG. 1).

The following table indicates the change in color of the reflected light as a function of thickness of the underlying layer (this table is provided as an example. It is based on a single layer silicon dioxide coating on an unpatterned wafer.

Similar tables can be generated for other material structures by, for example, making structures of differing thickness).

| Film Thickness (μm) | Color of reflected light |
|---|---|
| 0.05 | Tan |
| 0.07 | Brown |
| 0.10 | Dark violet to red violet |
| 0.12 | Royal blue |
| 0.15 | Light blue to metallic blue |
| 0.17 | Metallic to very light yellow green |
| 0.20 | Light gold or yellow slightly metallic |
| 0.22 | Gold with slight yellow orange |
| 0.25 | Orange to melon |
| 0.27 | Red violet |
| 0.30 | Blue to violet blue |
| 0.31 | Blue |
| 0.32 | Blue to blue green |
| 0.34 | Light green |
| 0.35 | Green to yellow green |
| 0.36 | Yellow green |
| 0.37 | Green yellow |
| 0.39 | Yellow |
| 0.41 | Light orange |
| 0.42 | Carnation pink |
| 0.44 | Violet red |
| 0.46 | Red violet |
| 0.47 | Violet |
| 0.48 | Blue violet |
| 0.49 | Blue |
| 0.50 | Blue green |
| 0.52 | Green (broad) |
| 0.54 | Yellow green |
| 0.56 | Green yellow |
| 0.57 | Yellow to "yellowish" (not yellow but is in the position where yellow is to be expected. At times it appears to be light creamy gray or metallic) |
| 0.58 | Light orange or yellow to pink borderline |
| 0.60 | Carnation pink |
| 0.63 | Violet red |
| 0.68 | "Bluish" (Not blue but borderline between violet and blue green. It appears more like a mixture between violet red and blue green and looks grayish) |
| 0.72 | Blue green to green (quite broad) |
| 0.77 | "yellowish" |
| 0.80 | Orange (rather broad for orange |
| 0.82 | Salmon |
| 0.85 | Dull, light red violet |
| 0.86 | Violet |
| 0.87 | Blue violet |
| 0.89 | Blue |
| 0.92 | Blue green |
| 0.95 | Dull yellow green |
| 0.97 | Yellow to "yellowish" |
| 0.99 | Orange |
| 1.00 | Carnation pink |
| 1.02 | Violet red |
| 1.05 | Red violet |
| 1.06 | Violet |
| 1.07 | Blue violet |
| 1.10 | Green |
| 1.11 | Yellow green |
| 1.12 | Green |
| 1.18 | Violet |
| 1.19 | Red violet |
| 1.21 | Violet red |
| 1.24 | Carnation pink to salmon |
| 1.25 | Orange |
| 1.28 | "Yellowish" |
| 1.33 | Sky blue to green blue |
| 1.40 | Orange |
| 1.45 | Violet |
| 1.46 | Blue violet |
| 1.50 | Blue |
| 1.54 | Dull yellow green |

Figure 14:
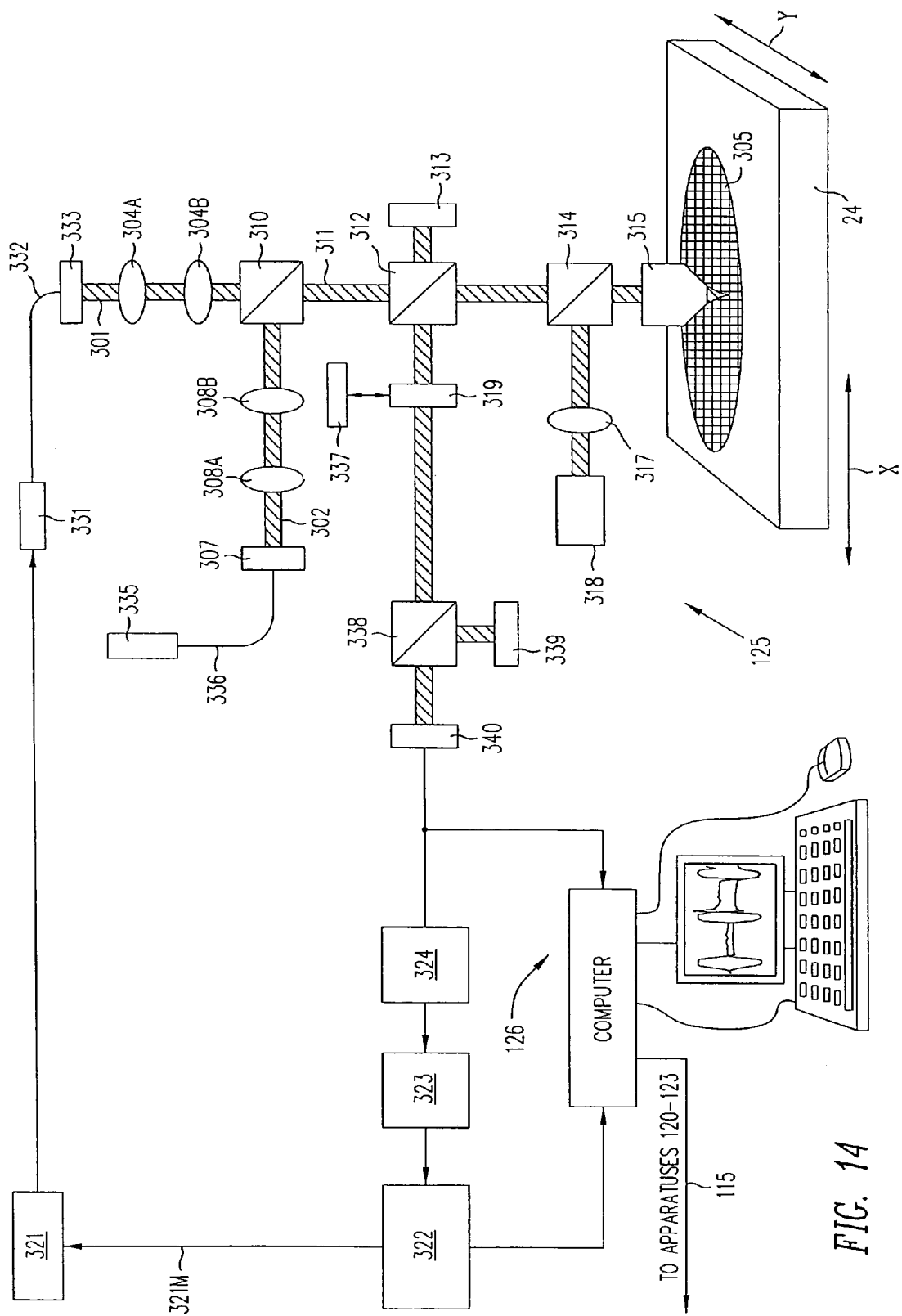
FIG. 14 illustrates, in a block diagram, one embodiment of a measurement apparatus of this invention.

For such a color measurement, the white light is polarized, as described in International Publication No. WO 01/67071 A2 mentioned above. Referring to FIG. 14, the following changes are made to implement this method: a beam splitter cube is inserted in the beam between lens 317 and beam splitter 314, and a white light source (such as a halogen lamp) is added to illuminate the new beam splitter. The new beam splitter injects the white light into the beam path.

Once the color is measured (either by human observation or by an optical instrument), the above table or a similar table may be used with the measured color to look up the thickness t. Note that thickness lookup is not necessary to measure voids, and in one embodiment, the above table is not used in the measurement process at all. Instead, such an embodiment monitors only uniformity of the oxide's thickness. However, thickness look-up could be performed in other embodiments, since it provides a rapid way to determine dielectric thickness over large areas, with high resolution (resolution is determined by the number of pixels in the image). Also, the above color table is only valid for a single layer of silicon dioxide over silicon. In practice, other dielectric materials might be used, or multiple layer films would be present, and the above table would have to be modified. An alternate embodiment reads out the color (e.g. red, green and blue values) from the camera, and correlates the read color to the thickness, which has been previously measured using a conventional measurement system such as an ellipsometer.

Another embodiment performs the following acts:
1. Thickness and index of refraction of each layer in the film is measured at a point outside but near the metal array, using a conventional instrument such as an ellipsometer.
2. The computer contains a model that may be created as follows. Once the thickness and index of refraction of each layer are known, the reflection at a known wavelength is calculated using conventional formulae. See, for example, Handbook of Optics, W. G. Driscoll and W. Vaughan editors, McGraw-Hill (New York) 1978, pp. 8–42 and 8–43. The color may be predicted using colormetric methods described in chapter 9 of the same book that is incorporated by reference herein in its entirety. The model which predicts the red, green and blue content of the reflection as a function of the measured index of refraction of each layer, the thickness of each underlying layer, and the thickness of the top layer. The measured color of the array is then compared to the predicted to determine the thickness of the top layer. This is the only layer that would vary in a polishing process, as the polish would not affect underlying layers.

Therefore, in certain embodiments, a relative difference in thickness is measured (either qualitatively or quantitatively) by comparing the colors obtained from two (or more) different regions of a structure, thereby to obtain a corresponding change in thickness of the layer in which the traces are embedded (only this layer would change with the process; the underlying layers are constant).

Figure 15:
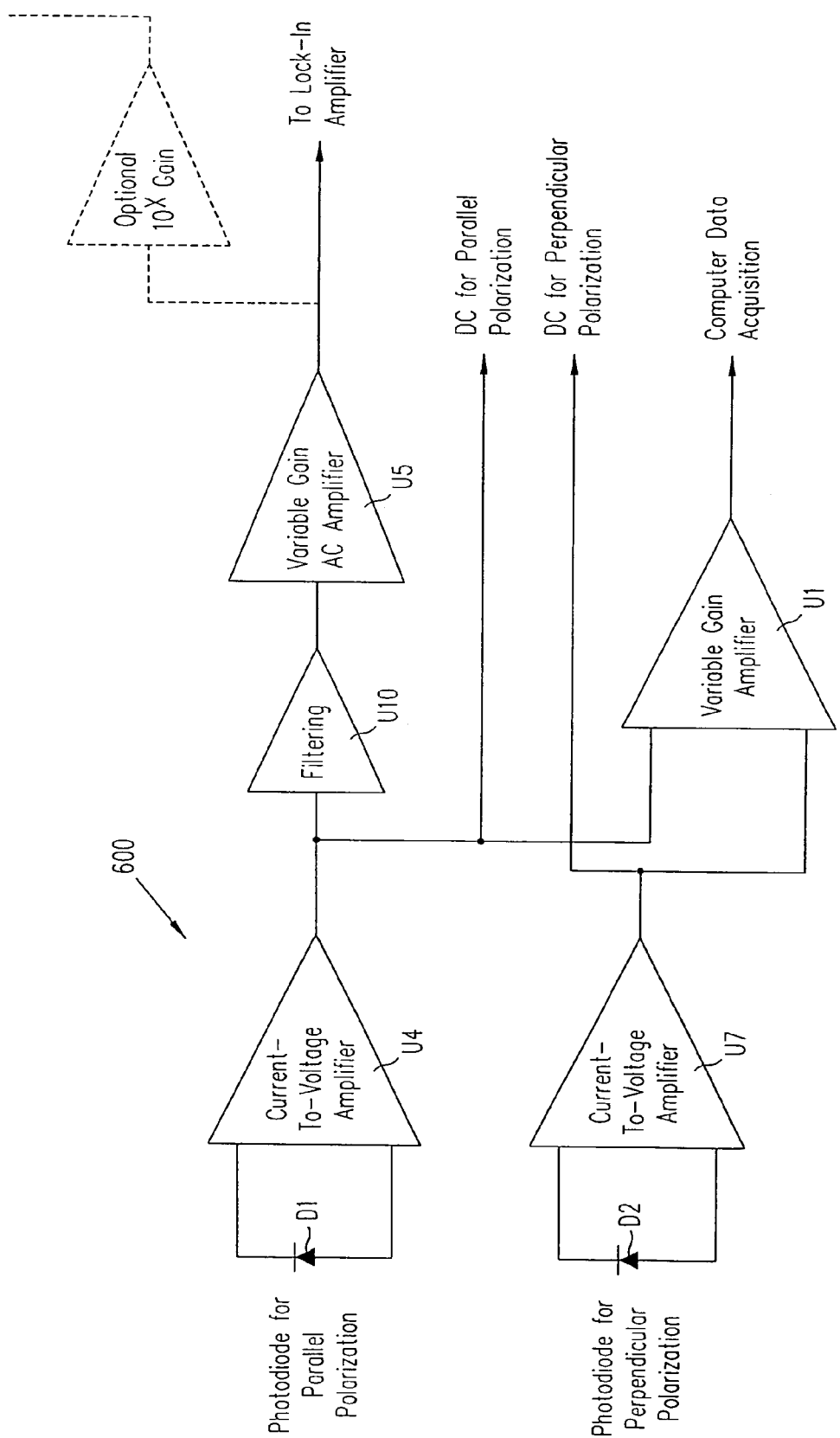
FIG. 15 illustrates, in a high-level block diagram, a circuit included in measurement apparatus of FIG. 14 in one embodiment.

In one implementation, one or more measurements of the type described herein are made by a circuit 600 (FIG. 15) that uses a photodiode (e.g. either of diodes D1 and D2 to generate a current (e.g. 1–2 milliamps) in response to the intensity of light incident on the photodiode. Thereafter, an amplifier U4 (FIG. 15) converts the current from the photodiode into a voltage (e.g. 2–4 volts). Amplifier U4 is coupled to a filter U10 that filters out high frequency noise (e.g. from power lines; e.g. U10 may suppress any signal outside the frequency range 100 Hz to 5 KHz). Thereafter, an amplifier U11 amplifies the varying component (also called "ac" component) of a measured signal by a gain that is selectable by the user (e.g. the gain may be any one of 1, 2, 4, 8, 16, 32, 64 and 128). The gain may be selected by the user depending on the structure that is currently under examination, and the type of signals being obtained from the measurement. If necessary, an optional 10× gain amplifier may be used to further amplify the measured signal. The resulting signal is provided to a lock-in amplifier for processing as described herein.

In another implementation, a signal from another photodiode D2 is amplified (as described above, but by amplifier U7). In addition to summing the measured signals, these signals can be compared to one another, e.g. by an amplifier U1 which provides a difference signal. The difference signal is proportional to a property of the wafer, such as surface roughness. In an alternative implementation, signals from each of amplifiers U4 and U7 are supplied to a summer (not shown) that in turn provides to filter U10 a signal that is the sum of the two signals obtained from the two photodiodes D1 and D2, for use as described herein.

Depending on the embodiment, beams 12 and 19 need not be coincident and in fact may be separated from one another e.g. in the longitudinal direction of traces 11A–11N if the effect of heating beam 19 can be measured across the separation distance. Moreover, the two signals S1 and S2 need not be measured simultaneously at the same location, and instead each of these signals can be measured individually and compared (or otherwise processed) to detect voids at a different time. For example, signal S2 may be measured several milliseconds after signal S1 and yet presence of voids detected as long as values for the same location are compared.

In another embodiment, acts of the type described herein are applied to a single metal line, either as an isolated line or as a line in an array of pitch comparable to or larger than the spot size. In this embodiment, measurements are performed using a scanning method, so that the position of the beam relative to the line is known. The scanning method eliminates the need for a vision system to perform automatic alignment. So a vision system that is unable to perform an alignment to the required tolerance can be used in this embodiment.

Figure 16B:
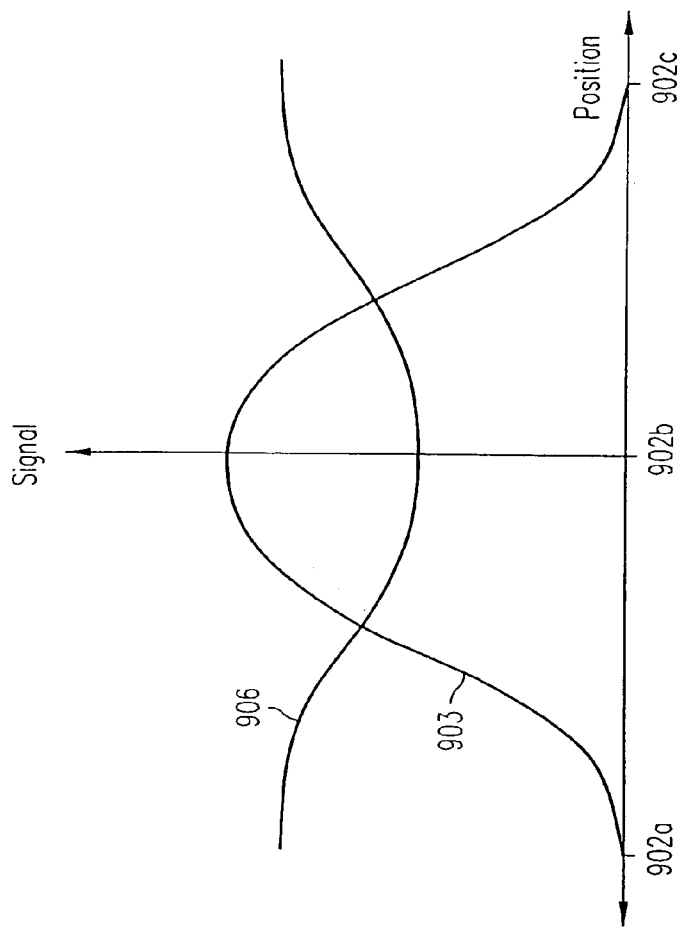
FIGS. 16A–16D illustrate, in drawings (FIGS. 16A and 16C) and graphs (FIGS. 16B and 16D), methods for measuring voiding in a single (isolated) metal line.
Figure 16A:
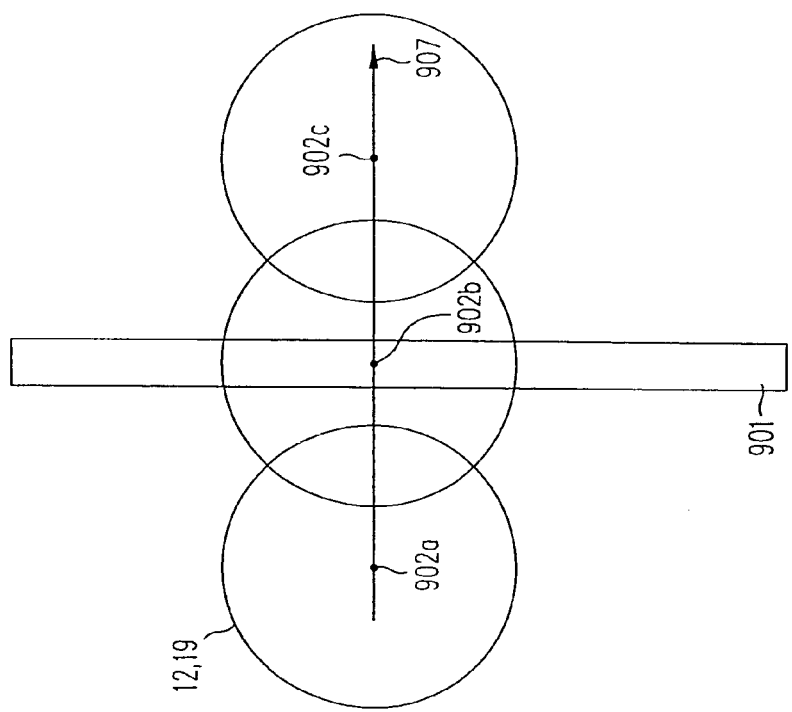
Figure 16D:
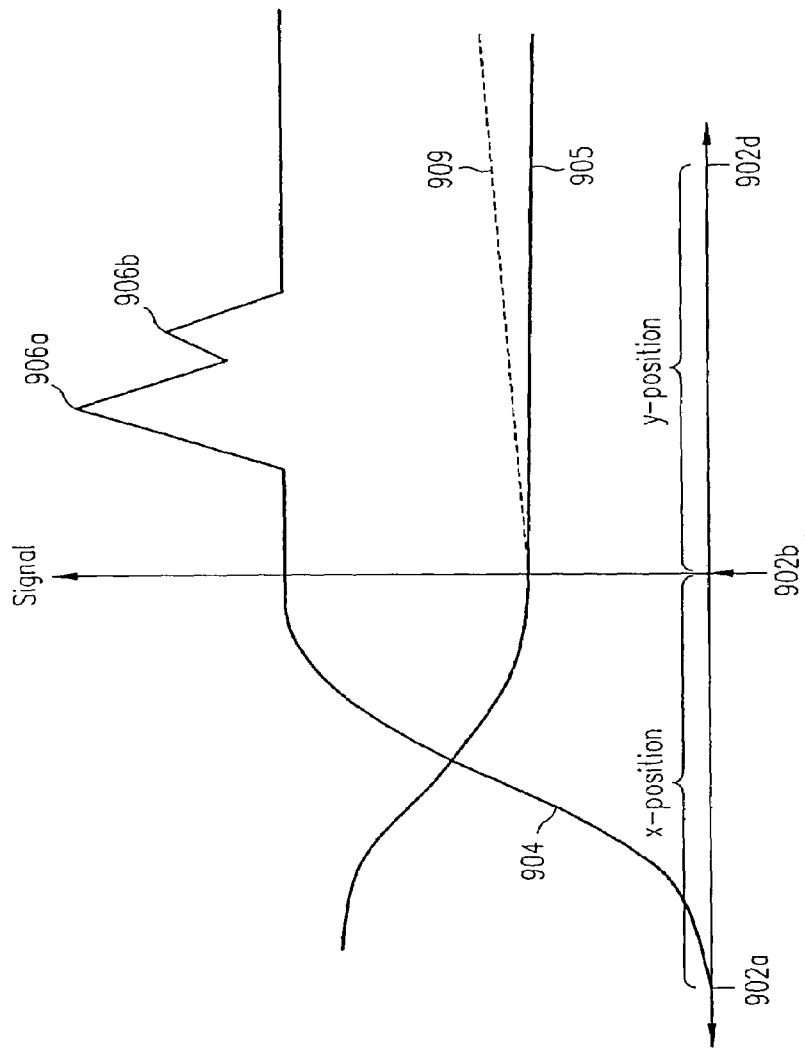
Figure 16C:
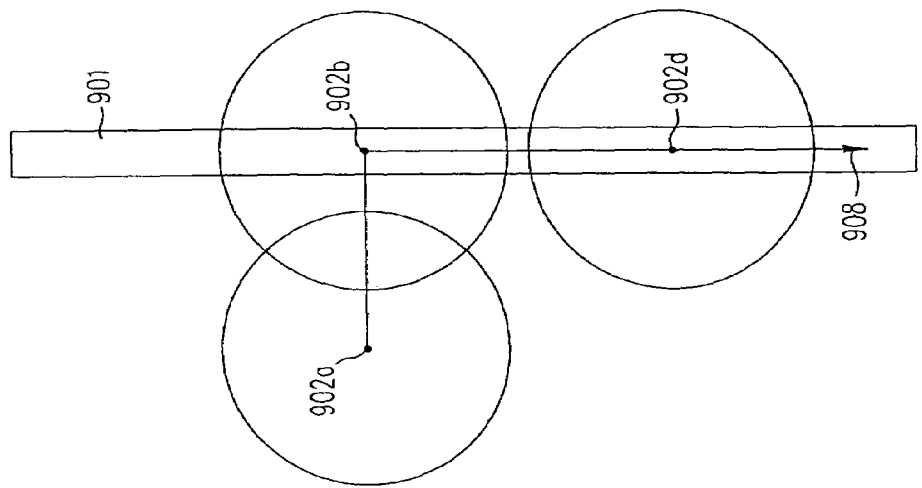

Specifically, probe beam 12 and heating beam 19 are initially coincident at a first position 902a (FIG. 16A) that is located sufficiently far away from trace 901 so that beams 12 and 19 do not overlap trace 901. At position 902a, a first signal 903 (see FIG. 16B) for the metal resistance measurement is zero, and a second signal 906 for the reflection measurement relating to the dielectric thickness has a non-zero value. Next, the two beams are scanned along arrow 907 (FIG. 16A), while remaining coincident with one another. First signal 903 reaches a maximum (FIG. 16B) when beams 12 and 19 overlay trace 901 (FIG. 16A) at a position 902b that is in the middle of trace 901, and falls back to zero (FIG. 16B) as beams 12 and 19 reach position 902c (FIG. 16A). Similarly, because trace 901 absorbs light, second signal 906 drops to a minimum at position 902b and returns to the original value at the other side of trace 901, at position 902c. In this case, signal profile 903 is read and compared to reflection profile 906. Changes in the relative height of signal 903 correspond to a potential voiding problem—that is, a void creates an obstruction in heat flow that increases the level of signal 903. If there was a void, then signal 903 in FIG. 16B has a higher value than a similar scan across another portion of the line lacking a void.

In the just-described method, positions 902a–902c were collinear (i.e. along a straight line). In a variant of the just-described method, beams 12 and 19 are scanned from a position 902a near trace 901 to a position 902b over trace 901, and thereafter along the length of trace 901 to a position 902d. Therefore, positions 902a, 902b and 902d are not collinear. In such an embodiment, first signal 904 (FIG. 16D) climbs in a manner similar to first signal 903 (FIG. 16B) until position 902b. At position 902b, the scan direction is the changed and beams 12 and 19 are moved along the length of trace 901, to position 902d. If there are no voids, then first signal 904 and second signal 905 remain constant during the travel along trace 901. However, any peaks 906a and 906b in first signal 904 during travel along trace 901 indicate a void. If second signal 905 trends up, as illustrated by dashed line 909, then the beams may be drifting off from trace 901. Therefore, the second signal 905 can be used to ensure that the beams remain aligned to trace 901.

Therefore, as illustrated in FIGS. 16A–16D, certain embodiments measure signals from a trace which is separated from other traces by at least the diameter of the beams, and interpret changes in the reflection properties as indicating the presence of voids under the trace. In these embodiments, the measurements are not in any sense averaged over multiple traces, and instead are actual measurements for the individual trace. Moreover, voids in a via chain may also be detected as discussed in the related Patent Application, "IDENTIFYING DEFECTS IN A CONDUCTIVE STRUCTURE OF A WAFER, BASED ON HEAT TRANSFER THERETHROUGH" filed by Peter G. Borden and Jiping Li. One or more acts of the type described therein may be used with one or more acts described herein, depending on the embodiment. Moreover, any acts of the type described herein may be performed in any order relative to one another, although depending on the embodiment, some acts may be performed in a specified order, for use in certain applications.

Furthermore, voids can be detected by measuring the same property at different locations, followed by comparison of the measurements from the different locations. For example, if signal S1 is being measured (see FIG. 3), then simply a change dS1 can be used to identify a deviation from baseline.

Numerous modifications and adaptations of the above-described embodiments, implementations, and examples are encompassed by the attached claims.

The invention claimed is:

1. A method for evaluating a structure that has a plurality of layers, the method comprising:
   measuring a first property of a first layer in the structure, to obtain a first measurement;
   measuring a second property of a second layer in the structure, to obtain a second measurement; and
   using the first measurement and the second measurement to determine existence of a void;
   wherein the first layer comprises a plurality of traces of conductive material supported by the second layer;
   wherein the measuring of first property is performed across a group of traces, thereby to obtain in the first measurement an average measure of the first property across traces in the group;
   wherein the measuring of first property comprises illuminating the structure with a beam comprising electromagnetic radiation having a wavelength greater than a pitch between two adjacent traces in said group; and wherein the first property is resistance per unit length of said traces.

2. The method of claim 1 wherein:

said second layer comprises a dielectric material and said second property is thickness.

3. The method of claim 1 wherein said using comprises:

displaying the first measurement and the second measurement in a graph as a function of location.

4. The method of claim 1 wherein said using comprises:

comparing the first measurement with the second measurement; and identifying a current location as having the void depending on an outcome of said comparing.

5. The method of claim 4 wherein said comparing comprises:

checking if the separation of said first and second measurements is greater than a predetermined amount.

6. The method of claim 4 wherein said comparing comprises:

comparing separation between the first measurement and the second measurement at the current location with a corresponding separation in another location.

7. The method of claim 4 wherein said comparing comprises:

checking if separation between the first measurement and the second measurement at the current location is approximately an order of magnitude greater than a corresponding separation in another location.

8. The method of claim 7 wherein:

the measurings at the locations are performed during a scan in a direction transverse to the plurality of traces and the group of traces is different in each of the locations.

9. The method of claim 1 wherein:

the first property is related to a dimension of the first layer; and the second property is related to a dimension of the second layer.

10. The method of claim 1 wherein:

at least one of the first property and second property is unrelated to a dimension.

11. The method of claim 1 further comprising:

prior to said measurings: etching grooves in the second layer, and forming the first layer by forming traces that fill the grooves at least partially; and subsequent to said using: adjusting a process used in creation of said structure if existence of said void is determined.

12. The method of claim 1 wherein:

the measuring comprises scanning said beam perpendicular to said group of traces.

13. The method of claim 1 wherein:

the measuring comprises scanning said beam perpendicular to a trace in said group up to said trace and scanning said beam along said trace.

14. The method of claim 1 wherein:

the electromagnetic radiation is polarized parallel to the group of traces.

15. The method of claim 1 wherein the beam is hereinafter "first beam," and the measuring of first property further comprises:

illuminating the structure with a second beam having intensity modulated at a predetermined frequency, the predetermined frequency being sufficiently small to ensure that heat generated in a region illuminated by the second beam transfers out of the region by diffusion.

16. The method of claim 15 wherein:

the second beam comprises electromagnetic radiation polarized in a direction parallel to the group of traces.

17. The method of claim 16 wherein the measuring of second property further comprises:

illuminating the traces with a beam comprising electromagnetic radiation polarized perpendicular to the group of traces.

18. The method of claim 15 wherein the first beam has a first wavelength, and the measuring of first property further comprises:

measuring an attribute of electromagnetic radiation of the first wavelength modulated at said predetermined frequency.

19. The method of claim 1 wherein the beam is hereinafter "first beam," and the measuring of first property further comprises:

focusing a second beam of electrons, said second beam having intensity modulated at a predetermined frequency.

20. The method of claim 1 wherein the measuring of second property comprises:

measuring electromagnetic radiation reflected by the second layer, the electromagnetic radiation being polarized perpendicular to said group of traces in the first layer.

* * * * *